US012796937B2

(12) United States Patent
Nikinmaa et al.

(10) Patent No.: US 12,796,937 B2
(45) Date of Patent: Nov. 17, 2026

(54) METHOD FOR DETECTING DENTAL PLAQUE USING INDOCYANINE GREEN

(71) Applicant: Koite Health Oy, Espoo (FI)

(72) Inventors: Sakari Nikinmaa, Espoo (FI); Tommi Pätilä, Espoo (FI); Juha Rantala, Espoo (FI)

(73) Assignee: Koite Health Oy, Espoo (FI)

( * ) Notice: Subject to any disclaimer, the term of this patent is extended or adjusted under 35 U.S.C. 154(b) by 1160 days.

(21) Appl. No.: 17/598,937

(22) PCT Filed: Mar. 30, 2020

(86) PCT No.: PCT/FI2020/050207
§ 371 (c)(1),
(2) Date: Sep. 28, 2021

(87) PCT Pub. No.: WO2020/193870
PCT Pub. Date: Oct. 1, 2020

(65) Prior Publication Data

US 2022/0167853 A1 Jun. 2, 2022

(30) Foreign Application Priority Data

Mar. 28, 2019 (FI) .................................... 20195246

(51) Int. Cl.
*A61B 5/00* (2006.01)
*A61K 49/00* (2006.01)

(52) U.S. Cl.
CPC .......... *A61B 5/0088* (2013.01); *A61B 5/0071* (2013.01); *A61B 5/0077* (2013.01);
(Continued)

(58) Field of Classification Search
CPC .................. A61N 5/062; A61N 5/0624; A61N 2005/0606; A61N 5/067;
(Continued)

(56) References Cited

U.S. PATENT DOCUMENTS 5,784,162 A 7/1998 Cabib et al.
9,700,211 B2 * 7/2017 Simons .................. A61C 19/04
(Continued)

FOREIGN PATENT DOCUMENTS

CN 1312959 A 9/2001
CN 102548466 A 7/2012
(Continued)

OTHER PUBLICATIONS

Olivi, Giovanni, and Maria Daniela Genovese. "Laser Applications for Caries Diagnosis and Prevention." Lasers in Restorative Dentistry: A Practical Guide (2015): Chapter 6, pp. 111-139. (Year: 2015).*
(Continued)

*Primary Examiner* — Serkan Akar
*Assistant Examiner* — Jason P Gross
(74) *Attorney, Agent, or Firm* — Laine IP Oy

(57) ABSTRACT

Method of detecting dental plaque, comprising the steps of subjecting a dental area of interest to high and low energy photons in the presence of a photosensitizer. The invention can be used antimicrobial and antiviral and antifungal detection and therapy. Thus, generally, viral or fungal infections in biofilm, plaque and on teeth surfaces can be detected and optionally treated. The method can also be used for detecting, determining or analysing the quantity or quality or both of the dental pellicle.

23 Claims, 4 Drawing Sheets

(52) U.S. Cl.
CPC .. *A61K 49/0034* (2013.01); *A61B 2562/0233* (2013.01); *A61B 2576/02* (2013.01)

(58) Field of Classification Search
CPC .... A61N 2005/0652; A61N 2005/0651; A61N 2005/0644; A61C 1/088; A61C 1/0046; A61C 5/40; A61C 5/50; A61C 8/0006; A61C 19/04; A61B 5/0088; A61B 2017/00057; A61B 5/0075; A61B 5/4547; A61B 1/043; A61B 1/0646; A61B 5/682; A61B 6/512; A61B 5/4552; A46B 15/0036; A46B 2200/1066; A46B 15/0034; A61K 2800/81; A61K 41/0057; A61Q 11/00; A61Q 11/02; G01J 3/2823; G01J 3/108; G01J 3/0218; G01J 2003/2826; G01N 21/359; G01N 2201/062
See application file for complete search history.

(56) References Cited

U.S. PATENT DOCUMENTS

| | | | | |
|---|---|---|---|---|
| 2004/0193235 A1* | 9/2004 | Altshuler | A61N 5/0603 | 607/88 |
| 2004/0193236 A1* | 9/2004 | Altshuler | A61N 5/06 | 607/88 |
| 2008/0038686 A1* | 2/2008 | Nagai | A61B 5/0088 | 433/29 |
| 2008/0058786 A1* | 3/2008 | Boyden | A61B 18/20 | 606/13 |
| 2008/0058908 A1* | 3/2008 | Bornstein | A61C 19/063 | 607/93 |
| 2008/0090198 A1* | 4/2008 | Liang | G01J 3/4406 | 433/29 |
| 2009/0087816 A1* | 4/2009 | Bornstein | A61C 1/0046 | 433/29 |
| 2011/0151394 A1* | 6/2011 | Rizoiu | A61K 8/25 | 433/29 |
| 2012/0172408 A1* | 7/2012 | Thyzel | A61K 6/69 | 548/427 |
| 2012/0310083 A1* | 12/2012 | Friedman | A61F 9/0079 | 600/431 |
| 2013/0323674 A1* | 12/2013 | Hakomori | A61B 1/043 | 433/29 |
| 2015/0010878 A1* | 1/2015 | Seibel | A61B 5/0088 | |
| 2015/0140502 A1* | 5/2015 | Brawn | A61C 19/06 | 433/29 |
| 2017/0303791 A1* | 10/2017 | Vermeulen | A61B 5/0075 | |
| 2018/0035896 A1* | 2/2018 | Nozaki | A46B 15/0036 | |
| 2018/0249913 A1* | 9/2018 | Seibel | A61B 5/0088 | |
| 2018/0252644 A1* | 9/2018 | Shi | G01N 21/6428 | |
| 2018/0318033 A1* | 11/2018 | Tesar | A61B 90/30 | |
| 2019/0076555 A1* | 3/2019 | Patil | A61K 49/0002 | |
| 2019/0167400 A1* | 6/2019 | Barnes | A46B 15/0012 | |
| 2019/0328234 A1* | 10/2019 | Seibel | A61B 5/7264 | |
| 2020/0093715 A1* | 3/2020 | Basa | A61K 8/361 | |
| 2020/0150041 A1* | 5/2020 | Harootunian | G01N 21/6456 | |
| 2021/0000567 A1* | 1/2021 | Sutter | A61C 1/0046 | |
| 2021/0263051 A1* | 8/2021 | Seibel | G01N 33/84 | |

FOREIGN PATENT DOCUMENTS

| | | | | |
|---|---|---|---|---|
| EP | 3267182 | A1 | 1/2018 | |
| JP | 2002515276 | A | 5/2002 | |
| JP | 2003210497 | A | 7/2003 | |
| JP | 2006521875 | A | 9/2006 | |
| JP | 2008532619 | A | 8/2008 | |
| JP | 2009534097 | A | 9/2009 | |
| JP | 2013135845 | A | 7/2013 | |
| JP | 2013535235 | A | 9/2013 | |
| KR | 100915718 | B1 | 7/2013 | |
| WO | WO9959462 | A1 | 11/1999 | |
| WO | WO WO2004084752 | A2 | 10/2004 | |
| WO | WO2005099563 | A1 | 10/2005 | |
| WO | WO2006098719 | A1 | 9/2006 | |
| WO | WO2007123880 | A2 | 11/2007 | |
| WO | WO WO2012005888 | A1 | 1/2012 | |
| WO | WO2013109978 | A1 | 7/2013 | |
| WO | WO2014097082 | A2 | 6/2014 | |
| WO | WO-2015082390 | A1 * | 6/2015 | A46B 15/0034 |
| WO | WO2016140199 | A1 | 9/2016 | |
| WO | WO2018081637 | A1 | 5/2018 | |

OTHER PUBLICATIONS

Giannelli, Marco, et al. "Treatment of severe periodontitis with a laser and light-emitting diode (LED) procedure adjunctive to scaling and root planing" Lasers in medical science 33.5 (2018): 991-1002. (Year: 2018).*

Liu et al. "Red fluorescence imaging for dental plaque detection and quantification: pilot study." Journal of biomedical optics 22.9 (2017) (Year: 2017).*

Stratonnikov, Aleksandr A., et al. "Application of backward diffuse reflection spectroscopy for monitoring the state of tissues in photodynamic therapy." Quantum Electronics 36.12 (2006): 1103 (Year: 2006).*

Lim, Hyun-Ju, and Chung-Hun Oh. "Indocyanine green-based photodynamic therapy with 785 nm light emitting diode for oral squamous cancer cells." Photodiagnosis and photodynamic therapy 8.4 (2011): 337-342 (Year: 2011).*

Desmettre, T., J. M. Devoisselle, and S. Mordon. "Fluorescence properties and metabolic features of indocyanine green (ICG) as related to angiography." Survey of ophthalmology 45.1 (2000): 15-27 (Year: 2000).*

Jun, Won, et al. "Microbial biofilm detection on food contact surfaces by macro-scale fluorescence imaging." Journal of food engineering 99.3 (2010): 314-322 (Year: 2010).*

Fekrazad, Reza, Kasra Karamifar, and Abbas Bahador. "Comparison of antibacterial effect of photodynamic therapy using indocyanine green (Emundo) with 2% metronidazole and 2% chlorhexidine gel on Porphyromonas gingivalis (an in-vitro study)." Photodiagnosis and photodynamic therapy 15 (2016): 28-33 (Year: 2016).*

Pourhajibagher, Maryam, et al. "Photo-activated disinfection based on indocyanine green against cell viability and biofilm formation of Porphyromonas gingivalis." Photodiagnosis and Photodynamic Therapy 17 (2017): 61-6 (Year: 2017).*

Info File SIROLaser Blue. Laser in Dentistry. Sirona (Year: 2018).*

Walsh, Laurence J. "New paradigms for assessing caries risk and lesion activity." Auxillary 5 (2011): 28-33. (Year: 2011).*

Bärenfaller et al: Effect of photoactivated disinfection using light in the blue spectrum. Journal of Photochemistry and Photobiology B: Biology, Mar. 8, 2016, vol. 158, pp. 252-257.

Paschoal et al: Photodynamic antimicrobial chemotherapy on*Streptococcus mutans*using curcumin and toluidine blue activated by a novel LED device. Lasers in Medical Science, Nov. 19, 2013, vol. 30, No. 2, pp. 885-890.

Gillenwater et al: Noninvasive diagnosis of oral neoplasia based on fluorescene spectroscopy and native tissue autofluorescence. Arch Otolaryngol Head Neck Surg, Nov. 1998, vol. 124, pp. 1251-1258.

Tsai et al: In Vivo Autofluorescence Spectroscopy of Oral Premalignant and Malignant Lesions: Distortion of Fluorescence Intensity by Submucous Fibrosis. Lasers in Surgery and Medicine, 2003, vol. 33, pp. 40-47.

* cited by examiner

METHOD FOR DETECTING DENTAL PLAQUE USING INDOCYANINE GREEN

FIELD OF INVENTION

The invention relates to plaque detection. In particular, the present method relates to a method of detecting dental plaque, comprising the steps of subjecting a dental area of interest to photons in the presence of a chemical agent which preferably contacts the plaque.

BACKGROUND

In biofilms microorganism are less susceptible to antimicrobials than bacteria in planktonic form. The mechanism behind the tolerance and resistance in biofilms includes slow penetration of antimicrobials through the biofilm matrix, altered microenvironment within the biofilm, different stress response of bacterial cells and the formation of sub-populations of so-called persister cells. In biofilms, potential resistance can be easily transferred among different species by horizontal gene transfer. It has been estimated that close to 80% of all microbial infections are caused by biofilms. This also relates to drug resistance where susceptible pathogen strains acquire resistance and selection of inherently less susceptible species make population more resistant.

Frequent biofilm infections include dental infections caused by dental plaque, as well as dermal infections, urinary tract infections, middle-ear infections, endocarditis and implant- or catheter-associated infections.

Successful antimicrobial treatment of microorganism in biofilms typically requires up to 100 to 1000 times higher concentrations of disinfectants or antibiotics than when treating their planktonic counterparts. For example, in a test, a 100 time greater concentration of amine fluoride and chlorhexidine was needed to kill monospecies biofilm of *Streptococcus sobrinus* than its planktonic counterpart. Similarly, *Escherichia coli, Pseudomonas aeruginosa* and *Staphylococcus aureus* required the application of 1000 time higher concentrations of antibiotics for effective treatment in biofilm compared to their planktonic form.

Dentists often have to combat antibiotic-resistant bacteria in periodontal or endodontic infections. It has been observed that resistance against disinfectants like chlorhexidine, the most common tool of dentists to treat oral infections, may correlate with antibiotic resistance.

Antibiotics have helped man to cope with bacterial infections to date, but the pathogens have become resistant to most of the antibiotics and the difficulty to develop new antibiotics threatens to return mankind to the pre-antibiotic era.

New antimicrobial strategies are therefore needed for example in dentistry in order to avoid excessive usage of antibiotics for treatment of periodontal, endodontic or mucosal topical infections caused by bacterial or yeast biofilms. One step necessary to achieve that end is to reliably being able to detect the presence of dental plaque.

SUMMARY OF THE INVENTION

It is an aim of the present invention to provide methods of detecting plaque present on dental surfaces of interest.

In particular, it is an aim to provide an approach for subjecting biological surfaces to light to enable a detection of the presence of a biofilm, such as plaque.

The present invention is based on the idea of detecting the presence of a biofilm in an area of interest comprising a biological surface by subjecting said area to a combination of high and low energy photons. It has surprisingly been found that the use, for example simultaneous use, of high and low energy photons on the target area of a surface will give an effect that is better than the use of such photons separately.

It would appear—although this is merely one possibility, and the scope of the present invention is not limited to the following explanation—that low energy photons will penetrate deep into the surface, whereas high energy photons will have an effect on the surface.

Thus, the same target area can be activated through photon up-conversion reactions where two or more photons are absorbed and cause the target molecule(s) to excite to a higher energy state.

In one embodiment, a method is provided wherein a dental area of interest area is contacted with a photosensitizer and the target area is subjected to the combination of first photons having a majority energy between 1.24 eV and 1.65 eV and second photons having a majority energy between 2.8 eV and 3.5 eV. Typically, said first and said second photons making up a majority, preferably more than 90%, of all photons directed towards the target area.

A further embodiment provides a photosensitizer for use in the detection of biofilm in the oral cavity of a mammal, wherein said sensitizer is applied to a dental area of interest and that area is subsequently or simultaneously subjected to first photons with a majority energy between 2.8 eV and 3.5 eV; and second photons with a majority energy between 1.24 eV and 1.65 eV.

A still further embodiment provides a kit for determination of biofilms comprising microbial, viral or fungal growth, in the oral cavity of a mammal, in particular on teeth surfaces and in mucous membranes, comprising an optoelectronic component and device thereof capable of simultaneously emitting a first light consisting of high energy and a second light consisting of low energy photons, said first and said second light amounting to at least 80% of all light emitted from the optoelectronic component or device, and at least one photosensitizer which can be activated by at least either of the high energy and low energy photons.

More specifically, the present invention is characterized by what is stated in the independent claims.

Considerable advantages are obtained. The use of high and low energy photons to target endo- and exogenous molecules gives rise to a target molecule site specific action due to low life-time of reactive or high energized oxygen.

According to the invention the high energy photons are being absorbed by endogenous (intracellular) molecules to generate reactive oxygen singlets and reactive oxygen. Simultaneously low energy photons are being absorbed exogenously (extracellular) by the photo-sensitizer resulting in reactive oxygen singlets and reactive oxygen.

The reactive oxygen singlets and reactive oxygen species will assist not only in the detection of biofilm but also in a subsequent inactivation, killing and otherwise reduction of micro-organisms such as bacteria, virus and fungus present in biofilm or plaque on teeth surfaces:

Thus, the present method of detecting biofilm, such as plaque, can be employed as a first step in a method involving further steps selected from the group of diagnosis and treatment and combinations thereof.

Thus, the treatment will achieve good tissue penetration. It makes it possible to give antibacterial treatment to different areas of pathogen at the same time as two or more different energy photons can target molecules in different areas. Different energy photons have also different tissue therapeutic and tissue stimulating effects. The combined high and low energy photons can affect bacterial communication as they might have deleterious effect in bacteriophages, which contain genetic material or other molecules. The light may also have effects in the production, formation or activating of such communicating molecules assessed as quorum sensing.

It appears that the high energy photons are typically being absorbed by species relating to or involved with the intracellular oxidative stress responses. They are therefore capable of disrupting pathogen treatment adaptation. One example of such a species is the flavin group of the peroxidase enzyme.

The high and low energy photons can be used with several different kinds of photosensitizers, wherein the activation can take place through different mechanisms such as heat generation, oxygen radicals and singlet oxygen. By utilizing treatment combination where pathogens are targeted with two or more unspecific yet fundamentally different mechanisms, efficient antibacterial treatment can be achieved. In one embodiment, ICG with low energy photons is used with high energy photons to give photo hyperthermia therapy (ICG acts 80% through heat generation and 20-15% through singlet oxygen formation) to pathogen membranes. High energy photons can be used for activating endogenous porphyrin molecules inherent in bacteria. Such molecules have high quantum yields and act mainly through singlet oxygen, resulting in localized oxidative bursts.

One important benefit of the combination of endogenous antibacterial therapy, in which the photons target inherent bacteria molecules, with exogenous photodynamic or photothermal therapy is that it can solve the issue that added exogenous photosensitizers tend to bleach out from target area during treatment.

The photosensitizer can be exhibit dental plaque specific binding to allow for early detection of plaque.

However, endogenous antibacterial light therapy is not limited to the presence of an exogenous photosensitizer.

Targeting the endogenous molecules inherent in bacteria with photons gives an effect which is independent of the photosensitizer attachment and uptake. This helps to balance the treatment so that areas with less photosensitizer will have as good treatment as the areas with more photosensitizer. The photo bleaching effect of endogenous antibacterial therapy to pathogen endogenous molecules has also antipathogenic function as these molecules are essential for the pathogen unlike the added exogenous photosensitizer.

In long term, the targeting of bacteria endo- and exogenously gives the best effect in vivo against many bacteria as effectivity of exogenous treatment is limited to photosensitizer attachment and/or intake to target pathogen.

For example, simultaneously absorbing 1.53 eV and 3.06 eV photons can excite endogenous porphyrins creating antibacterial effect in addition to tissue healing effect. The high energy photons reduce the formation of biofilm extracellular polysaccharides matrix which gives synergies with exogenous PDT and reduces pathogenicity of biofilms.

Different photosensitizer, photon energy and treatment parameters can be used to target different age biofilms in different part of its life cycle. The composition of, for example, dental plaque and biofilms varies from individual to individual. People with low incidence of caries show different bacterial amounts, different species and different phylogenetic diversity within the dental plaque, when compared to individuals with high incidence of caries, especially in the early days of plaque formation.

With the present technology people can be efficiently treated, irrespective of whether they are of high or low caries incidence.

The present method will typically achieve auto-fluorescence which refers to, in particular, inherent fluorescence in dental plaque. Further, it will typically also achieve photosensitizer fluorescence, which refers to fluorescence of an external photosensitizer. Preferably it will achieve fluorescence based on both auto-fluorescence and fluorescence.

Thus, auto-fluorescence is generated by old plaque. It is a characteristic of plaque.

Fluorescence is generated by the photosensitizer.

This dual action of plaque, can be used in plaque analysis. Measuring firstly the auto-fluorescence of the plaque using 405 and/or 810 peak LEDs with or without specific filtering, and secondly measuring the absorption of light by ICG with or without combining the light emission of ICG.

Using the present method for detecting plaque is advantageous because it also opens for reliable instrumental detection assisting visual assessment of the presence of plaque, as carried out by a dentist or other dental professional, or potentially replacing such detection entirely, for example allowing for the individual to make the detection him- or herself.

The present method allows for imaging of plaque based on fluorescence, absorption or auto-fluorescence. It further allows for determination of intensity based on fluorescence, reflectance of light, auto-fluorescence or total intensity or combinations thereof.

The present method of detection can also be employed for the detection and determination of biofilms and discoloration and plaque to assist in cosmetic treatment of teeth surfaces.

Next embodiments will be examined in more detail with reference to the attached drawings.

EMBODIMENTS

Definitions

Figure 1:
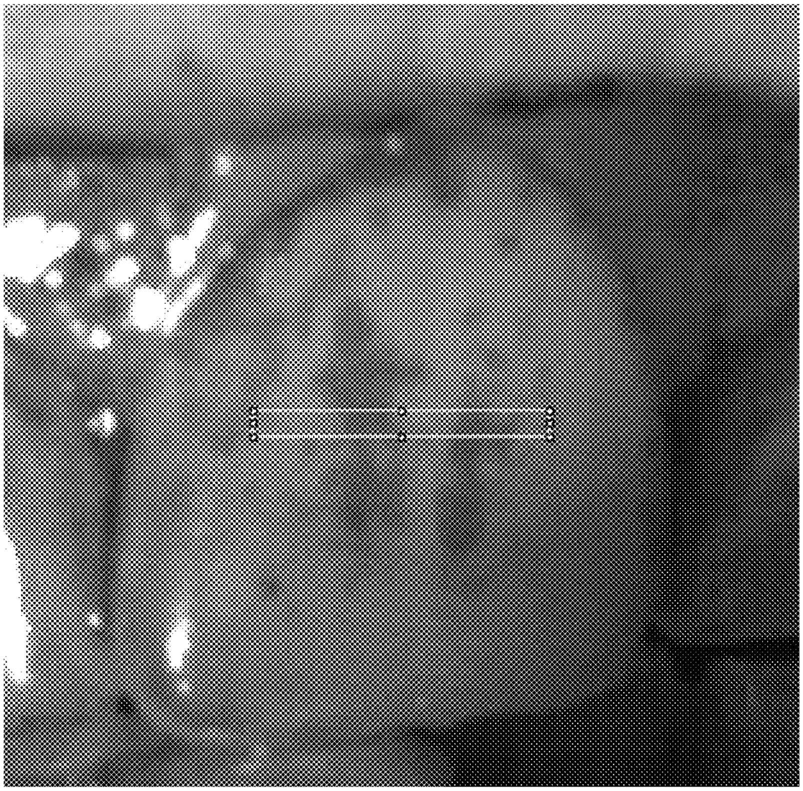
FIG. 1 is a photograph showing dye plaque specificity as observed in room light with hamamatsu 1394 and NIR light source.

In the present context, "photodynamic therapy", also referred to by the abbreviation "PDT", stands for any therapy where light is converted to some form of reactive oxygen.

"Plaque" is used synonymously with "dental plaque" for referring to biofilm or a mass of bacteria that grows on dental surfaces, in particular surfaces in the oral cavity (mouth) of mammals. Typically, plaque grows on teeth surfaces. As known in the art, plaque is primarily colorless but may take up colour, e.g. due to tartar formation, thus forming a cosmetic detriment. Plaque is commonly found on various surfaces of the teeth and also along the gumline and even lower, below the gumline in cervical margins. Bacterial plaque is considered one of the major causes for dental decay and gum disease.

"Dental pellicle", or "acquired enamel pellicle" (abbreviated "AEP") stands for an acellular biofilm formed by proteins, carbohydrates, and lipids that adsorb onto the enamel surface. The AEP is formed by saliva, oral bacterial debris and exoenzymes as well as gingival crevicular fluid (CRF). Gingival crevicular fluid provoies plasma proteins in the pellicle. The composition of AEP can be changed in oral diseases, especially caries and periodontis. The inflamed gingiva can change the composition of the AEP to a direction which enables more pathogenic bacteria to attach to pellicle to form the plaque. The AEP forms within minutes on teeth and serves as the landing area for bacteria for later plaque development.

Plaque and dental pellicle removal can be carried out as a cosmetic treatment.

Examples of "reactive oxygen" includes singlet oxygen, oxygen radicals and oxygen ions.

"Antimicrobial photodynamic therapy", also referred to by the abbreviation "aPDT", is a photochemistry-based method that uses photons to activate "sensitizers" that, in the activated state, impart antimicrobial effect.

"Benefit agents" are typically chemical compounds or substances which have a beneficial effect on the tissue or treatment effect. Such compounds are exemplified by the following: host defense peptides, enzymes, hydrogen oxide producing enzymes, certain pH liquid, acid, base, antibacterial enzymes, honey, hydrogen peroxide, resin, Trolox, EDTA, D-vitamin, antigens, hormones, prolactin, hydroscopic material, alpha tocopherol, verapamil, sodium bicarbonate, sodium chlorite, pomegranate, aloe vera, chamomile, curcumin, aquacumin, baking soda, sea salt, turmeric, activated charcoal, lemon juice, coconut oil pulling, peppermint oil, spearmint oil, cinnamon oil, DMSO, titanium dioxide, calcium carbonate, carrageenan, sodium lauryl sulfate, sodium monofluorophosphate, benzyl alcohol, *Mentha piperita* oil, Petroselinum sativum oil, sodium benzoate, bromelain, papain, maltodextrin, citric acid, Limonene, silica, *Mentha piperita* extract, glycerin, nettle extract, bicarbonates.

"Antimicrobial blue light", also referred to by the abbreviation "aBL", is light, typically in the wave length area of 405 to 470 nm, that exhibits intrinsic antimicrobial effect without the involvement of exogenous photosensitizers.

"Photosensitizers" are compounds or molecules that are capable of absorbing electromagnetic radiation for example in the ultraviolet or visible region and transferring it to adjacent molecules. Typically, the photosensitizers have de-localized $\pi$ systems.

The photosensitizers can be naturally occurring compounds ("natural photosensitizers") and synthetic compounds. Examples of natural photosensitizers include the following: Hypericin, curcumin, phenalenone derivatives, Cercosporin, psoralen, xanthotoxin, Angelicin, alpha-Terthienyl, Phenylthepatriyne, THC, Cannabidiol (CBD). Synthetic photosensitizers include the following: RB (Rose Bengal), MB, Porphyrin derivatives, Curcumin derivatives, Methylene Blue, Indocyanine Green, Erythosine, Phenalenone derivatives, Fullerene derivatives, Xanthene derivates.

In a preferred embodiment, "plaque specific photosensitizers" are used. The term "plaque specific" designates photosensitizers which preferentially bond or adsorb to dental surfaces containing or coated with plaque compared to dental surfaces which are at least essentially free from plaque. Thus, when exposed to dental surfaces, more plaque specific photosensitizer is gathered on the plaque-containing surfaces than on the plaque-free surfaces ((per surface units). Typically, the concentration (per square unit) is more than 10%, in particular more than 20%, preferably at least 30% and for example 40% or more greater on plaque surfaces than on plaque-free surfaces of plaque specific photosensitizers.

Further, in embodiments, for plaque specific photosensitizers, light absorption or fluorescence of the administered photosensitizer is higher in plaque when plaque imaging light is used.

The term "adsorb", when used in conjunction to bonding or adhering of the photosensitizer to oral surfaces or biofilms or plaque, respectively, includes any kind of attachment or binding of the photosensitizer and is typically based on the formation of physical or chemical bonds or combinations thereof.

A particular preferred sensitizers is Indocyanine Green (in the following abbreviated "ICG").

The term "potentiating substances or agents" stands for agents which are capable of enhancing the effect or activity of other agent(s) so that the combined effect of them is greater than the sum of the effects of each one alone.

Examples of "potentiating substances or agents" includes ions, ion scavengers, surfactants, oxygenated compounds, reactive oxygen producing compounds, organic and inorganic salts, divalent ions, pigments, antimicrobial peptides, EDTA, immunostimulants and antibiotic or other antimicrobial compounds described but not limited to chlorhexidine.

"Exogenous" when used in relation to bacteria stands for "outside" of the bacteria "Endogenous" stands for "inherently present" in the bacteria. When used with reference to molecules and substances in the bacteria, "endogenous" is used interchangeably with the term "intracellular".

In the present context, "mammals" have the conventional meaning in the art. Particularly interesting targets are humans and animals kept for husbandry and as pets, including dogs, cats, rabbits, horses, cattle, sheep, goats and pigs.

"Non-coherent" when used in connection to light means that the amplitude and phase of the emitted light waves fluctuate randomly in space and time. One embodiment comprises using LEDs as non-coherent light sources. Another embodiment comprises using UVC lamps as non-coherent light sources.

"High energy photons" are photons with energy in the range from 3.5 eV to 2.8 eV, in particular about 3.2 to 2.9 eV or 3.17 to 2.95 eV. Typically, such photons are contained in light having a wavelength in the range of about 350-450 nm, for example about 390 to 410 nm.

"Low energy photons" are photons with energy in the range from 1.24 eV to 2.48 eV, in particular 1.3 to 2.4 eV, for example 1.4 to 1.6 eV or 1.45 to 1.56 eV. Typically, such photons are contained in light having a wavelength in the range of about 500 to 1000 nm, for example about 780 to 830 nM.

Light with photons having "a majority energy in the range from 3.5 eV to 2.8 eV" stands for light, for example in the form of a light beam or light ray, in which at least 50%, in particular at least 60% or at least 70% or at least 80% or at least 90% or at least 95%, of the photons—as indicated by their energy—have an energy in the range from 3.5 eV to 2.8 eV.

Light with photons having "a majority energy in the range from 1.24 eV to 2.48 eV" stands for light, for example in the form of a light beam or light ray, in which at least 50%, in particular at least 60% or at least 70% or at least 80% or at least 90% or at least 95%, of the photons—as indicated by their energy (or wavelength)—have an energy in the range from 1.24 eV to 2.48 eV.

In the present context, a specific value of a wavelength will typically include a range about that specific value, for example of 5 to 20, in particular about 10 to 15 nm, on either side of the value. Thus, for example, "405 nm" will be considered to include a range of wave lengths of about 395 nm to 415 nm, i.e. 405 nm±10 nm. Similarly, "810 nm" will be considered to include a range of wavelengths of about 395 nm to 825 nm, i.e. 810 nm±15 nm.

Generally speaking, it has been found that simultaneous dosing of both high and low energy photons, in particular together with a low energy photon activated photosensitizer, increases the antimicrobial effect of light compared to dosing of either group of photons separately. This can be seen in planktonic forms of microbes, but especially in biofilms, when applied as a single dose.

The use of both high and low energy photons is disclosed in our co-pending patent application FI20185904, filed on 26 Oct. 2018.

High and low energy photons can, as will be discussed in the following embodiments, also be used in detection of plaque.

Basically, the present method of detecting dental plaque comprises the steps of subjecting a dental area of interest to high and low energy photons in the presence of a photosensitizer. Typically, in a first step, a photosensitizer is adsorbed to dental area of interest, and then the dental area of interest is subjected to high energy photons and low energy photons, respectively. In one embodiment, a plaque specific photosensitizer or a mixture of at least one plaque specific photosensitizer and other photosensitizers is adsorbed to dental area of interest and subsequently dental area containing adsorbed photosensitizer is subjected to high energy photons and low energy photons.

In one embodiment, the dental area of interest is subjected to high energy photons and low energy photons, respectively, simultaneously. In another embodiment, the dental area of interest is subjected to high energy photons and low energy photons sequentially.

One embodiment comprises directing high energy photons and low energy photons to a dental area of interest to achieve both auto-fluorescence and fluorescence of the area, and detecting, preferably separately detecting, the auto fluorescence and fluorescence generated in response to the high energy photons and the low energy photons, respectively. In one embodiment, auto-fluorescence generated by natural intracellular and extracellular fluorophores is detected.

One embodiment comprises subjecting a dental area exhibiting early plaque to low energy photons and subjecting a dental area exhibiting old biofilm comprising intracellular and extracellular fluorophores porphyrin molecules to high energy photons.

In one embodiment, a combination of first light having a wavelength of 405 nm±10 nm and second light having a wavelength of 810 nm±15 nm is used, both the first and the second lights comprising non-coherent light, for example produced by optoelectronic devices, such as light emitting diodes (LEDs).

In one embodiment, a combination of first light having a wavelength of 405 nm±10 nm, second light having a wavelength of 810 nm±15 nm, and third light having a wavelength of 780 nm±10 nm is used, the first, the second and the third lights comprising non-coherent light, for example produced by optoelectronic devices, such as light emitting diodes (LEDs).

In one embodiment, a combination of first light having a wavelength of 405 nm±10 nm, second light having a wavelength of 810 nm±15 nm, third light having a wavelength of 780 nm±10 nm, and fourth light having a wavelength of 830±15 nm, is used, the first, the second the third and fourth lights comprising non-coherent light, for example produced by optoelectronic devices, such as light emitting diodes (LEDs).

In embodiments of the present technology preferably the photosensitizer is selected from the group of plaque specific sensitizers, which sensitizers typically adhere preferentially to dental surfaces containing plaque than to dental surfaces not containing plaque. Such photosensitizers are represented by Indocyanine Green ("ICG").

Indocyanine green is a particular preferred photosensitizer suitable for use, for example in conjunction with the afore-mentioned combination of first, second, and optionally third and optionally fourth light.

In one embodiment, the step of contacting the dental area of interest comprises adsorbing the photosensitizer to the dental area from a liquid composition, such as a mouth rinse, which contains the photosensitizer. As an example, the liquid composition may contain 0.00001 to 10%, in particular 0.0001 to 0.1% by weight of the photosensitizer.

One embodiment comprises detecting auto-fluorescence and/or fluorescence from the dental area of interest by using a filter positioned in the light path from the dental area of interest to a detector, such as an observer's eyes or detector component(s) of an instrument.

As an example can be mentioned the use of a specific filtering of 405/780/810/830 nm light to enhance detection of fluorescence and/or auto-fluorescence, or detection of ICG light absorption or light emission abilities or their change.

405 and 810 peak light emitting diodes cause fluorescence in old dental plaque. When ICG is added to this plaque, without any filtering, this plaque is absorbing light, instead of emitting light.

One embodiment comprises detecting absorption of light of one, two, three or four different wavelengths and comparing the peak absorption of the light. In one particularly preferred embodiment, ICG absorption for light having a wavelength of 780 nm and light having a wavelength of 810 is detected and the ratio between the peak absorption is determined.

One embodiment comprises detecting fluorescence or auto-fluorescence emission caused by excitation of absorption of one, two, three or four different wavelengths and comparing peak emission of light. In one particularly preferred embodiment porphyrin and flavin fluorescence caused by 405 nm±10 nm excitation is measured at 455 nm, 500 nm 582 nm and 622 nm and compared to ICG emission excited at 810 nm±10 nm and measured in the range of 820 to 850 nm. Second particularly preferred embodiment, ICG emission having an excitation wavelength of 780 nm and measured emission in the range of 800 to 820 nm and having an excitation wavelength of 810 nm and measured emission in the range of 820 to 850 nm.

Figure 8:
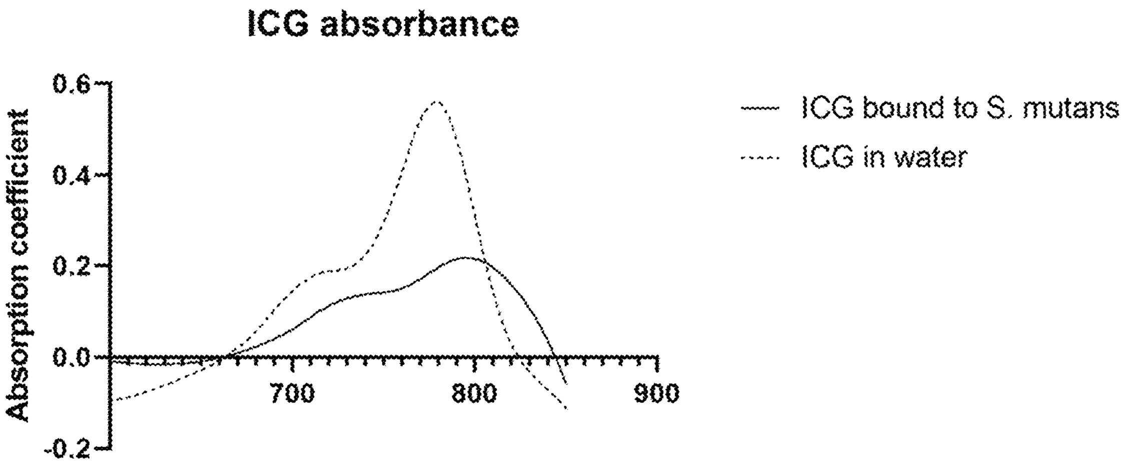
FIG. 8 is a chart showing the absorbance of ICG as a function of the wavelength of incident light.

The ICG will redshift 20 nm upon binding to bacterial (FIG. 8), thus measuring the ratio of free ICG vs. bound ICG the degree of bacteria binding can be detected. Dental plaque bacterial composition changes during plaque age and early plaque does not cause substantial auto-fluorescence of 405 nm light but is still well visible with ICG plaque imaging. Comparing excitation of ICG and auto-fluorescence of 405 nm to 450 nm information on bacterial biofilm age and thickness and bacteria composition can be obtained.

Information of absorption or emission and emission ratio of free ICG and bound ICG, and 405 nm auto-fluorescence can be used to guide and focus treatment carried out with at least two different wavelengths, as explained above, "dual-light treatment", to target area and in order to change the ratio between emitted lights to increase treatment effectivity against certain type of biofilm. Further treatment progression can be followed by measuring decline in 405 nm and/or 810 nm absorption or subsequent fluorescence emission. Measurement information can be fed back to device/user and treatment parameter such as intensity, light ratio, duration, resubmission of external photosensitizer can be altered/signaled.

In one embodiment a photosensitizer, in particular ICG, is subjected to external stimulus and changes in its emission and absorption characteristics are observed.

In one embodiment, external stimulus can be provided by biological means, like administering sugary solution, to stimulate bacteria acid formation in biofilm or with external actuator applying external electrical field, magnetic field, acoustic energy, force or electromagnetic radiation. Thus, in one embodiment, at a first point of time, a first image is taken of the teeth, at a second point of time, after the first, the individual is allowed to gargle or rinse the teeth with a solution containing sugar, and at a third point of time, after the second point of time, a second image is taken of the teeth.

In particular ICG can be used to measure the acid forming capacity of dental biofilm by following change in biofilm formation upon administering carbohydrate solution to dental biofilm and measuring change in absorption and emission characteristics of ICG caused by pH change in biofilm.

Specific filtering of 405 and/or 810 nm light can be used to enhance detection of auto-fluorescence, or detection of ICG light absorption or light emission abilities. The filtering can be located in front of the illuminating LED light source, or in front of a camera unit. The filtering can be low pass, high pass or band pass filtering or any of their combinations.

Thus, one or several auto-fluorescence can be detected and the information thereof combined.

The filters can also be positioned in between the observer's eyes, and the light emitting plaque. The filters can be located for example in eye glasses, where the filters are installed in eyeglasses' frames and provided as a kit with the light source to enable detection of the dental plaque.

It is also possible to use dual wavelength light and near infrared sensor to monitor old and new plaque. High energy photons absorb and excite phorphyrine molecules that allow detection of old plaque and detection of low energy photon absorption to early dental plaque with NIR camera allows the detection of early dental plaque.

Thus, a filter can be provided which can be located in front of the illuminating LED light source, or in front of a camera unit. In one embodiment, filtering is carried out using one or more filters selected from the group of low pass filters, high pass filters, band pass filters and combinations thereof.

Detection can be carried out by detecting auto-fluorescence at one or several wavelengths and optionally combining information obtained by detecting auto-fluorescence at several wavelengths. Typically, the dental area of interest is subjected to first light having a peak wavelength of about 405 nm, comprising high energy photons, and to second light having a peak wavelength of about 810 nm, comprising low energy photons.

One embodiment comprises

- subjecting the dental area of interest to light having a peak wavelength of about 405 nm or 810 nm or both, optionally sequentially;
- measuring first autofluorescence generated by the dental area of interest in response to such light, optionally using filtering to distinguish predetermined auto-fluorescence; then
- subjecting the dental area of interest to light having a peak wavelength of about 405 nm or 810 nm or both, optionally sequentially, in the presence of a plaque specific photosensitizer;
- measuring second auto-fluorescence generated by the dental area of interest in response to such light, optionally using filtering to distinguish predetermined auto-fluorescence; and
- determining the ratio of the first and the second auto-fluorescence.

Typically, the adsorption rate, and optionally the photobleaching rate, of the plaque specific photosensitizer is determined.

In one embodiment, fluorescence ICG will be determined in a wavelength range which corresponds to a redshift of about 10 to 30 nm, for example 20 nm, from the light of the emitted light.

One embodiment comprises measuring the ratio of free ICG to. bound ICG in order to detect the degree of bacteria binding.

As discussed above, dental plaque bacterial composition will change dependent on plaque age and early plaque does not cause substantial auto-fluorescence of 405 nm light but is still well visible with ICG plaque imaging.

In one embodiment, excitation of ICG and auto-fluorescence of 405 nm to 450 nm are compared in order to determine one or several parametres of the bacterial biofilm.

In particular, one or several parameters selected from biofilm thickness, biofilm density, biofilm bacterial composition, pH of the biofilm and combinations thereof, of the dental area of interest.

Based on the above, in one embodiment, the dental area of interest is subjected to light having a peak wavelength of 405 nm, 780 nm and 810 nm, and the light absorption by the plaque specific photosensitizer is determined.

One embodiment comprises measuring a first absorption of light of free plaque specific photosensitizer in liquid phase, measuring a second adsorption of the plaque specific phtosensitizer to the dental area of interest, and determining a least one parameter selected from biofilm thickness, biofilm density, biofilm bacterial composition, pH of the biofilm and combinations thereof, of the dental area of interest.

The pH of the bacteria biofilm can be determined based on the shift in the absorption spectrum of the plaque specific photosensitizer.

One embodiment comprises measuring plaque specific photosensitizer fluorescence at light having a peak wavelength of about 810 nm and light having a peak wavelength of about 830 nm, and determining the ratio the fluorescence for determining value of free ICG and bound ICG and for detecting sites of antibacterial activity.

In any of the above embodiments, hyperspectral imaging or spectroscopy can be used for plaque detection or analysis.

An image can be generated by using a sensor and preferably an algorithm.

In one specific embodiment, external stimulus to dental plaque is given in form of electromagnetic radiation, electric field, chemical or mechanical energy or a combination of them while monitoring changes in fluorescence properties.

In one embodiment, light or fluorescence intensity is measured (fluorescence intensity, total intensity, reflected intensity, auto fluorescence intensity).

In addition to plaque, the present technology can also be applied to detect and determine or analyze the quantity and/or quality of the dental pellicle" using high or low energy photons. Thus, one embodiment provides a method of detecting, determining or analysing the quantity or quality or both of the dental pellicle, comprising the steps of subjecting a dental area of interest to high and low energy photons in the presence of a photosensitizer.

Acquired enamel pellicle (AEP), analysis as a potentially important adjunct in salivary diagnostics. Thus, it is highly beneficial that the present technology can be used to collect pellicle and that it also provides a good yield and ideally removes all (or essentially all) organic material present on the tooth surface.

Based on the foregoing, a kit for detecting biofilm, such as dental plaque, on teeth surfaces, comprises for example an optoelectronic device capable of simultaneously emitting a first light consisting of high energy and a second light consisting of low energy photons, said first and said second light amounting to at least 80% of all light emitted from the optoelectronic component or device, and at least one photosensitizer which can applied to the teeth surfaces, capable of absorbing to said biofilm and of being activated by at least either of the high energy and low energy photons.

Typically, optoelectronic device is capable of emitting high energy photons with majority energy between 2.8 eV and 3.5 eV and low energy photons with majority energy between 1.24 eV and 1.65 eV, together with a photosensitizer or a plurality of photo-sensitizers.

In one embodiment, the optoelectronic device comprises a light emitting component that has two or more light emitting surfaces (EPIs), together with a photosensitizer or a plurality of photosensitizers.

Typically, the device comprises a sensor capable of detecting light emitted by fluorescence or auto-fluorescence and of producing a detection signal corresponding to the fluorescence or auto-fluorescence detected.

The optoelectronic device can be provided in the shape of a tooth brush, or the shape of a mouth piece which can be inserted in a mouth between the biting surfaces of the teeth, or the shape of a rod like illuminator.

Further, the optoelectronic device used may comprise micro-spectrometer sensors, temperature sensors, light sensors, pH sensors, force sensors, gyroscopes, pressure sensors or combinations thereof.

In one embodiment, the photosensitizer is provided in form of a water soluble effervescent tablet, gel, or paste, and further comprising a one-time use mouth piece and light applicator. In one embodiment, the photosensitizer is provided in the form of water soluble effervescent tablet and the kit comprising a hand held light applicator capable of emitting dual light photons.

Typically, the optoelectronic device is capable of emitting light, in particular non-coherent light, at a first wavelength from 400 to 430 nm, preferably at a dosage of 1 to 120 $J/cm^2$, and in particular with a power density of from about 10 to about 2500 $mW/cm^2$ for a period of time from 0.5 s to 120 min, and at a second wavelength from 780 to 830 nm, preferably at a dosage of 1 to 120 $J/cm^2$, and in particular with a power density of from about 10 to about 2500 $mW/cm^2$ for a period of time from 0.5 s to 120 min.

In particular, the optoelectronic device comprising light-emitting diode(s) (i.e. LEDs) as a light source.

The present technology can be used in a method wherein detection of biofilms, such as plaque, on tooth surfaces is incorporated in a sequence of steps including diagnosis and treatment, in particular antimicrobial treatment, or a combination thereof. Further, the present method of detecting biofilms can be carried as a first step of such a sequence of steps, followed by diagnosis and/or treatment (in particular antimicrobial treatment). It can also be carried out as an intermediate step or as the final step of a sequence comprising steps for diagnosis and/or treatment (in particular antimicrobial treatment) or biological surfaces, in particular teeth.

Thus, in one embodiment the present technology is used for evaluating the effect of antimicrobial treatment.

With regard to the generation and use of high and low energy photons (i.e. "dual light treatment") in detection of plaque and AEP, reference is further made to the following discussion, which primarily relates to the use of such photons in treatment of biofilms.

The treatment using low energy photons together with an exogenous photosensitizer, as practiced in dentistry, tends to lose its efficacy in a biofilm in the long term. There are many reasons for this resistance formation, including activation of genes responsible of influx pump expression. Irrespective of the actual cause, or combination of different explanations, similar phenomena have been encountered when continuing daily dosing of high energy photons in biofilm studies in the context of the present invention.

The improved efficacy of the dual light treatment, as a single dose, and the ability of the treatment to sustain the efficacy, can be explained by simultaneous generation of radical oxygen species by light in the presence of endogenous and exogenous sensitizers. The endogenous sensitizers are photoreactive molecules within the cell. These molecules can be for example proteins containing amino acid side chains or proteins bound to chromophoric prosthetic groups, such as flavins and heme.

In one embodiment, chromophore bound proteins are in key roles of cell function including electron transfer reactions in mitochondria and their oxidation may have deleterious effects.

Damage in the side chain containing proteins may play a significant role in bystander damage. On the other hand, exogenous sensitizers have an ability of achieving rapid and efficient production of radical oxygen species damaging both cell membrane and cell wall structures and when entering the cell, damaging other structures. Targets for reactive oxygen species in biological surface include DNA, RNA, proteins, lipids and sterols.

In a first embodiment, the present technology provides for a method of treating biological surfaces with electromagnetic radiation in the form of light of two different energy levels, a first light with photons having a majority energy in the range from 3.5 eV to 2.8 eV and a second light with photons having a majority energy in the range from 1.24 eV to 2.48 eV. The treatment is carried out by simultaneously directing the photons of the first light and the second light against the biological surface.

As referred to above, generally the term majority energy means that more than 50%, in particular more than 60%, for example more than 70% or more than 80% of the energy of the light lies in the indicated range.

In one embodiment the photons have at least 50% of their energy at 3.17 eV to 2.95 eV and 1.56 eV to 1.45 eV, respectively.

In one embodiment, non-coherent radiant light energy is generated at least two different energy levels, a first and a second energy level;

from the non-coherent radiant light energy there is provided first light having a wavelength corresponding to the majority energy of the first energy level, and second light having a wavelength corresponding to the majority energy of the second energy level; and the first and second light is then simultaneously directed against the biological surface.

In one embodiment, the light is generated using an optoelectronic component and device thereof, which is capable of simultaneously emitting a first light consisting of high energy and a second light consisting of low energy photons, the first and second light amounting to at least 80% of all light emitted from the optoelectronic component or device.

By the light discussed above, endogenous and exogenous excitement of the biological material of the surface is achieved, preferably so as to generate reactive oxygen singlets or reactive oxygen species or both.

By the treatment, biological contamination of surfaces, such as microbial or viral or fungal contamination of biological tissues can be prevented or combatted. The treatment can be used for cosmetic purposes as well as for antimicrobial and antiviral and antifungal therapy.

The light can be used as such or it can be combined with a photo-sensitive substance (a photosensitizer) for the purpose of photodynamic therapy (PDT). This will be discussed in more detail below.

In one embodiment, the high energy photons and low energy photons are applied in conjugation with at least one exogeneous photo-sensitizer, which can be activated with the low energy photons.

In one embodiment, a photo-sensitive substance (a photosensitizer) is provided for use in topical treatment of mammal tissues, wherein the sensitizer is applied to a superficial part of the tissue, such as on mammal skin or on a mucous membrane and the part thus treated is subsequently or simultaneously subjected to light at two different wavelengths, viz. to first light having high energy photons with a majority energy between 2.8 eV and 3.5 eV; and a second light having low energy photons with a majority energy between 1.24 eV and 1.65 eV).

In such an embodiment, the high energy photons are being absorbed by endogenous (intracellular) molecules such as porphyrin or riboflavin with photon energy of 2.48 eV or higher to generate reactive oxygen singlets and reactive oxygen. Simultaneously, low energy photons are being absorbed exogenously (extracellular) by the photo-sensitizer resulting in reactive oxygen singlets and reactive oxygen. Both endogenously and exogenously generated reactive oxygen singlets and reactive oxygen species can inactivate, kill or otherwise reduce the levels of micro-organisms, such as bacteria, virus and fungus, in tissue, biofilm, saliva, skin, plaque and teeth surface and mucous membranes.

In one embodiment of invention the high energy photons are being absorbed by intracellular oxidative stress response mechanisms, such as peroxidase enzyme's flavin group, and thus disrupting pathogen treatment adaptation.

In another embodiment, at least one photo-sensitizer is contacted with micro-organisms, such as bacteria, virus and fungus, in a target, such as tissue, in biofilm, saliva, skin, plaque and on teeth surfaces and mucous membranes, by applying it on the target with a carrier. Thus, the photo-sensitizer(s) can be applied in the form of an aqueous solution, an alcohol containing solution, a hydrophilic gel, a hydrophobic gel, a hydrophilic polymer, a hydrophobic polymer or in the form of a paste, lotion, tablet, tape, plaster or band-aid.

It would appear that high energy photons and low energy photons penetrate to different depths into micro-organisms or into tissue, biofilm, saliva, skin, plaque and teeth surface and mucous membranes. Thus, by the present technology reactive oxygen singlets and reactive oxygen species are generated at different depths in targets, such as in tissues, biofilms, saliva, skin, plaque, teeth surface and mucous membranes, thus inactivating, killing or otherwise destructing, or at least reducing the content of, micro-organisms, such as bacteria, virus and fungus.

As will be shown in the examples with particular reference to one species of gram positive bacteria (*Streptococcus mutans*), the present technology is effective against bacteria. Thus, generally, gram positive bacteria are represented by the genera *Streptococcus*, e.g. *Streptococcus pyogenes, Streptococcus agalactiae, Streptococcus dysgalactiae, Streptococcus bovis, Streptococcus anginosus, Streptococcus sanguinis, Streptococcus suis, Streptococcus mitis*, and *Streptococcus pneumoniae, Staphylococcus*, e.g. *Staphylococcus aureus, Staphylococcus epidermidis, Staphylococcus simulans, Corynebacterium, Listeria, Bacillus, Clostridium, Rathybacter, Leifsonia*, and *Clavibacter.*

One further group of bacteria to be targeted by the present technology is represented by gram negative bacteria, such as bacteria of the phyla Proteobacteria, Aquificae, Chlamydiae, Bacteroidetes, Chlorobi, Cyanobacteria, Fibrobacteres, Verrucomicrobia, Planctomycetes, Spirochetes, Acidobacteria, Actinobacteria, Firmicutes, Thermotogae, *Porphyromonas* and Chloroflexi. Specific examples include the following: *Escherichia coli, Salmonella*, such as *Salmonella enteritidis, Salmonella typhi, Shigella, Pseudomonas, Moraxella, Helicobacter, Stenotrophomonas, Bdellovibrio, Neisseria gonorrhoeae, Neisseria meningitidis, Moraxella catarrhalis, Haemophilus influenza, Klebsiella pneumoniae, Legionella pneumophila, Pseudomonas aeruginosa, Escherichia coli, Proteus mirabilis, Enterobacter cloacae, Serratia marcescens, Helicobacter pylori, Porphyromonas gingivalis, Aggregatibacter actinomycetemcomitans* and bacteria of the genus *Acinetobacter*, for example *Acinetobacter baumannii, Acinetobacter albensis* and *Acinetobacter apis.*

The treatment is also effective against viruses, such as Adenoviruses, Herpesviruses, Poxviruses, Parvoviruses, Reoviruses, Picornaviruses, Togaviruses, Orthomyxoviruses, Rhabdoviruses, Retroviruses, Papillomavirus and Hepadnaviruses.

Treatment has also shown effectivity against fungus such as *Candida* species in particular *Candida albicans.*

As discussed below in detail, the photo-sensitizer can be mixed with a carrier to provide the photo-sensitizer in the form of a solution, gel, paste, lotion or even plaster, tape, tablet or band-aid capable of application on the biofilm or infected area of target tissue or other biological surface. The photo-sensitizer is typically applied for example in liquid form as a gel in amounts of about 0.01 mg/ml to 10 g/ml, for example 0.1 mg/ml to 1 g/ml.

In one embodiment, a method according to any of the above embodiments is carried out using an anti-microbial optoelectronic component and device thereof by simultaneously emitting high energy photons absorbed by endogenous molecules and low energy photons absorbed by exogenous molecules.

In a further embodiment, the anti-microbial optoelectronic component and device thereof, used in a method according to any of the above embodiments, is emitting high energy and low energy photons and feed-in voltage or current is alternated or pulsed at 1 Hz to 1 GHz frequency independently from each other.

In a further embodiment, the anti-microbial optoelectronic component and device thereof, used in a method according to any of the above embodiments, is simultaneously emitting high energy (in the range of 2.48 eV and 1.24 eV) photons and low energy photons (in the range of 3.5 eV and 2.8 eV). According to this embodiment the optoelectronic device may comprise an optional photo detector to detect photo luminescence of the endogenous and exogenous molecules or their photo decomposition side products.

An embodiment comprises an optoelectronic component and device thereof having a plurality of semiconductor chips that are connect in series or in parallel, the chips exhibiting emission energy that can be varied in the range of 2.48 eV and 1.24 eV and in the range of 3.5 eV and 2.8 eV, respectively.

The area of the target to be treated can vary. In one embodiment, the area is about 0.1 $cm^2$ to 4 $cm^2$. Such a limited treatment area is typical for topical treatment, for example for treating parts of a mammal's skin or other areas exhibiting infection or biofilm or both. In another embodiment, the treatment area is about 10 to 100 $cm^2$. This area applies to situations of tooth treatment, which can be reached by using a mouth piece.

The power or wattage to be directed towards the target area varies typically in the range of 0.01 W to 500 W, in particular about 0.1 to 50 W, for example 1 to 25 W.

In one embodiment, light is directed to the target area at 0.001 $W/cm^2$ to 2 $kW/cm^2$, preferably 0.01 $W/cm^2$ to 20 $W/cm^2$, in particular about 0.050 $W/cm^2$ to about 10 $W/cm^2$.

As a result of the treatment, there is typically a temperature increase in the target area. In one embodiment, the temperature increase varies in the range of about 0.1 to 20° C., for example 0.2 to 10° C. and in particular about 0.5 to 5° C. The localized peak temperature in specific treatment site can exceed before mentioned values for limited time (typically less than 30 sec, in particular less than 15 sec).

In an embodiment according to the invention an optoelectronic device is used in a method of producing and delivering photodynamic radiant energy for preventing or for therapeutically treating diseases comprising the steps of

- (i) generating a non-coherent radiant light energy at multiple energy levels;
- (ii) providing a media or molecules capable of absorbing at least a part of the radiant energy;
- (iii) delivering light energy in substantially exact light energy wavelength needed to photoactivate the media or molecules capable of absorbing at least a part of the radiant energy; a preventing or therapeutic disease treatment; and
- (iv) preventing or therapeutically treating a target by endogenously, exogenously or both endogenously and exogenously generating reactive oxygen singlets and reactive oxygen species in said target.

One embodiment of the invention is that the optoelectronic device is used for programmed cell death of pathogenic micro-organisms, such as bacteria, virus or fungus, controlled by combination of high and low high photons and endogenous photosensitive compound or multiple different of compounds.

As mentioned above, in one embodiment, the light treatment of any of the above embodiment is carried out by way of photodynamic therapy (PDT). Such therapy comprises light and non-toxic target molecule that is activated by light. The target molecule absorbs a photon's energy and achieves an excited state. The target molecule can then exit this state by emission of a photon (fluorescence light), emission of heat or forming so called triplet state. This triplet state can then react with oxygen through charge transfer (type I reaction) or by transferring energy (type II reaction). In type I mechanism, charge is transferred to a substrate or to molecular oxygen generating reactive oxygen species like hydrogen peroxide and oxygen radicals like superoxide ions or free hydroxyl radicals. In type II mechanism, energy only—not charge—is transferred directly to molecular oxygen, whereby the highly reactive singlet oxygen ($^1O_2$) originates.

The antimicrobial effect of PDT is based on an oxidative burst upon illumination and relies on damage to cellular structures and molecules, therefore being an unspecific mechanism. This burst is immensely reactive and thus having short below 0.3 micrometers effective range thus making the treatment location specific.

The ratio between different action mechanism and the activation wavelengths is target molecule specific thus PDT, PTT and PHT treatment must be engineered specifically for certain light and target molecule compositions. Some photosensitizers or target molecules have higher ability to generate heat and others react through triplet state formation. For example, Indocyanine green (ICG) releases over 80% of absorbed energy as heat but porphyrins have singlet oxygen quantum yield between 0.5 to 0.8. Thus, selection of photosensitizer(s) will also define the classification of the treatment to photodynamic, photothermal or photo hyperthermia as the exact mechanism of pathogen killing can vary.

Photothermal effect is related to local heating of the pathogen. One possible approach of pathogen killing is to use pathogen selective heat generating photosensitizer with proper wavelength to locally heat the target pathogens. Its widely known that biofilms have lower cooling capability compared healthy tissue as they lack active blood circulation and thermal conductivity.

In addition to exogenous photosensitizer activation the administered photons can affect pathogens through interactions with pathogen endogenous molecules. Flavin and porphyrin photoreaction is crucial in blue light induced intrinsic mechanism to kill the bacteria.

There are several bacterial counterparts to plant phototropins, the blue-light sensing flavin binding proteins and/or iron-free porphyrins. Three major classes of flavin photosensors in bacteria, LOV (Light, Oxygen, Voltage) domains, BLUF proteins (Blue Light sensing Using flavin adenine dinucleotide, FAD) and cryptochromes regulate diverse biological activities in response to blue-light.

The bacterial LOV-proteins exhibit a variety of effector domains associated to the light-responsive LOV-domain, e.g. histidine kinase, transcriptional regulators, putative phosphodiesterase's and regulators of stress factors, pointing to their physiological role as sensing and signaling proteins. Thus, the application of certain energy photons might alter the bacterial response to the given therapy. A considerably large number of the bacterial LOV proteins are members of the histidine protein kinase superfamily. Histidine kinases are multifunctional, and in bacteria typically transmembrane proteins of the transferase class of enzymes that play a role in signal transduction across the cellular membrane. For example, bacterial influx pumps, responsible in drug resistance can be histidine kinases. Histidine kinase receptor activation can be located in periplasmic-sensing, transmembrane-sensing or cytoplasmic-sensing.

BLUF proteins can control the expression of genes related to photosynthesis through a light-sensitive proteins, which interact with a DNA-binding protein. Many BLUF proteins carry an extra domain downstream from the BLUF domain, with enzymatic or other properties, and the majority of these proteins appear to be homodimers. A protein called BlrP1, for example, is a dimeric cyclic nucleotide phosphodiesterase from *Klebsiella pneumonia* that shows a fourfold increase in enzyme activity under light conditions. AppA and PAC are just two examples of many photosensitive proteins carrying the BLUF domain, about 100 amino acid residues long, that is responsible for the detection of light, these are called "group 1" proteins. Many other BLUF proteins have fewer than 200 amino acid residues and are designated "group II" proteins. These proteins have little more than the BLUF domain in each subunit, but may carry secondary structural elements in the C-terminal region that are required for stability.

Photolyases and cryptochrome blue-light photoreceptors are evolutionarily related flavoproteins that perform distinct functions. Photolyases repair UV-damaged DNA in many species in bacteria similar to cryptochromes.

In antiviral treatment the viral population is targeted simultaneously with three or more antiviral drugs.

In antifungal treatment, the fungal population is targeted simultaneously with one, two, three or more antifungal drugs.

As described above in one embodiment, a treatment is carried out that combines exogenous effect to sites of administered benefit agent(s) that can consist of cell wall structures, EPS matrix, cell to cell signaling and endogenous effect where pathogen internal molecules are affected in their functional surroundings.

This treatment targets key functional sites and outer and internal membrane structures creating oxidative burst that is difficult to control by bacteria oxidative stress response mechanisms and temperature stress to further destabilize cell wall and cytoplasmic membrane. Described wide scale attack goes far beyond traditional PDT as the pathogen & pathogen population is attacked in different sites with oxidative and temperature burst exogenously and endogenously.

PDT, PHT and PTT can be potentiated also by adding active molecules or disinfectant compounds that breach cell wall structures, disinfectants capable of altering cell wall stability, external heating of target area, use of singlet oxygen scavenger that can act as reactive oxygen transporters, use of ion scavengers that removes divalent ions and thus destabilizes bacteria cell wall of gram negative bacteria, use of ion pump inhibitors to increase endogenous concentration of photosensitizer, applying immune response stimulators, microbial efflux pump inhibitors, protein transport e.g. porins stimulators, applying antibiotics to reduce pathogen viability and use of antibiotic or antibacterial substance as photosensitizer or in conjunction with the photosensitizer.

One embodiment comprises using during a first period of time a first photosensitizer and during a second period of time a second photosensitizer, which is different from the first photosensitizer. Typically, the first photosensitizer and the second photosensitizer can be activated using first light and second light, respectively. Preferably, first and second photosensitizers are used in combination, or alternatingly or at least one of them is used at a predetermined point of time during the treatment.

In one embodiment, the first photosensitizers are selected from the group comprising high energy photon activated photosensitizers ("type-I photosensitizers"), whereas the second photosensitizers are selected from the group comprising low energy photon activated photosensitizers ("type-II photosensitizers").

One potential approach to treatment is to adjust the treatment ratio of type I and type II mechanisms based on observed efficacy during treatment. Treatment can combine I and II mechanism at same time or rely more on one of the mechanisms and add/replace the compound working through the other mechanism in specific intervals to further increase the treatment efficacy.

For example, combining type-II photosensitizer with low energy photons and high energy photons with episodic addition of type-I photosensitizer or a pigment that generates reactive oxygen through charge transfer processes. One possible combination is to combine type II photosensitizer indocyanine green with type I photosensitizer curcumin with high and low energy photons. Treatment can also be monitored and the mechanism to be changed when a specific event is detected.

In one embodiment, treatment potentiation is achieved by pulsing the light to allow replenishment of target molecules, such as oxygen, during the dark periods, or by adding extra target molecules to treatment, such as super oxygenated water or oxygen generating compounds for example hydrogen peroxide. This embodiment in particular aims at increasing the amounts oxygen present to enhance the effect of the photodynamic therapy.

The wait time between pulses can be 0.01 to 100 times the length of the treatment pulse. This is particularly important as the maximum treatment power is limited by heat generation and heat dissipation. Treatment is more effective and time needed for treatment shorter if the light is delivered in a way that allows generation of active oxygen.

Use of high and low energy photons is beneficial as the different energy photons have different tissue stimulating properties. Low energy photons can have beneficial tissue heating of 2.7 degrees to a depth of 2 cm. This increases oxygen partial pressure and blood circulation that subsequently stimulates the metabolism of the cells including the promoted immune reaction.

High energy photons, particularly photons with an energy of 3.06 eV, have endogenous bacteria killing effects but the penetration of this wavelength to tissue is limited. These same target molecules can be activated through a photon up-conversion reaction where two or more photons absorb simultaneously to excite the target molecule to a higher energy state.

In one embodiment, the selection of 3.06 eV and 1.53 eV is a particularly good combination. 1.53 eV nm has exactly ½ of the photon energy of that of 3.06 eV but it has much higher tissue penetration. Thus, by subjecting the target to simultaneous absorption of 1.53 eV photons and 3.06 eV photons, can excite endogenous porphyrins creating antibacterial effect in addition to tissue healing effect. High energy photons reduce the formation of biofilm extracellular polysaccharides matrix which synergies with exogenous PDT and reduces pathogenicity of biofilms.

The invention is suitable in treatment of conditions caused by pathogens, like bacteria, virus and/or fungus, on skin, in the mouth, on the surface of teeth, gums, mucosal membranes, throat and genitals.

The method can also be carried out such that light only is used for tissue stimulating purposes.

The PDT treatment is nonspecific and thus generating resistance against it is inherently difficult. The robustness of PDT treatment can be increased by using different types of photosensitizers that work through singlet oxygen, charge transfer as well as heat generation. The aspect of heat induced pathogen killing, photothermal therapy, is fundamentally even more robust than PDT. These two techniques have synergistic effect which makes combination of these highly effective system.

Even as the treatment is highly robust the selectivity of more treatment withstanding bacteria species will happen. In oral setting this can be mitigated by focusing treatment to area of interest and leaving other areas untreated. This will keep changes to mouth flora minimal compared to antibacterial mouthwashes and provide efficient bacterial killing in the site of interest, for example surfaces of teeth and gums.

Light system can also include tissue stimulating light such as near infrared that has deep penetration into tissue and which is known to stimulate blood circulation and immune response.

Light can also be used to stimulate teeth bone formation and device heat can be used to increase the fluoride binding to enamel in addition of potentiating PDT and PTT treatment.

Device has important function as heat generating surface that increases the treatment effect and increases the fluoride binding rate it also helps the fluoride and photosensitizer to penetrate deeper into biofilm through thermal diffusion. This further increases the treatment effectivity.

The biofilm metabolism and bacteria composition changes when biofilm ages from 0 hours to mature biofilm of 96 hours old. This sets pressure to PDT treatment as different ages of biofilm 0, 12 h, 24 h, 32 h, 48 h, 72 h and 96 h require different treatment for most efficient overall treatment outcome.

In the present technology it is preferred that the photosensitizer is specific for biofilm, making its inherent optical and light properties (reflection, absorption, fluorescence, transmission, bleaching) a mean to detect and measure bacteria biofilm properties such as coverage and thickness.

The absorbed light will also heat the target tissue thus making possible to measure tissue health by comparing temperature difference in different tissue locations. In particular by heat monitoring it's possible to detect cancer tissue or inflammation, as they have lower cooling capability compared to healthy tissue. Absorption and time dependent bleaching and fluorescence intensity can be used to measure the biofilm thickness and bacteria amount thus making possible better follow disease state or overall health of the target area. Monitoring is particularly useful to monitor chronic periodontitis and gum health, and in early detection of cancers.

For treatment monitoring purposes and for safety of continuous treatment the photosensitizer can have selectivity to target tissue resulting in higher light absorption in target biofilm compared to clean dentin or healthy tissue when monitored with fluorescence microscope set to monitor the absorption maximum of the photosensitizer. Monitoring data can be used to adjust treatment to adapt changes during treatment, such as bleaching of one or more photosensitizers or direction of power to high biofilm areas or plan a personalized treatment options such as more frequent use, guide to focus mechanical cleaning to certain area or recommend an expert visit.

Mineralization process can be monitored with different light absorption and emission of sites going through remineralization and sites where enamel is disappearing. Particularly use of blue light together with NIR light allows simultaneous detection of deeper cavities as well as surface changes of the tooth and enamel.

Indocyanine green goes through red shift upon binding to pathogens, it is possible to quantify and characterize biofilm and its total amount by measuring red shift and the rate of photobleaching. The total absorption and rate of photobleaching corresponds to thickness of biofilm and to amount of active substance in the biofilm. Furthermore, spectrometer analysis can be used to detect plaque properties, such as sugar levels, pH-levels, fats, calorie content, protein content, amount of extracellular polymetric substance in biofilm. For these purposes the optoelectronic device used in treatment can incorporate micro-spectrometer sensors, temperature sensors, light sensors, pH sensors, force sensors, gyroscopes, pressure sensors.

Two or more photons can absorb simultaneously to give rise to super excited state that have distinct fluorescence and chemical properties. The energy of super excited state is higher than the normal excitation state. The rate of super excited state formation can be used quantify biofilm thickness and detect pathogens deeper in the tissue.

As described before the treatment effect can be potentiated by inhibition of microbial efflux pumps, affecting biofilm external and internal EPS matrix, affecting outer structures of pathogen, through disruption of pathogen to pathogen communication or quorum sensing, providing higher concentration or oxygen or reactive oxygen to target site, stimulating immune response, promoting oxidative stress transfer, use of enzymes, increasing active substance uptake into pathogen and biofilm, addition of chemical quenchers of singlet oxygen (carotenoids, Beta-carotene, and alpha-tocopherol) Addition of inorganic salts, particularly potassium iodide, addition of divalent ions, antimicrobial peptides, disinfectants, carrier liquid and antibiotics. Photons can be used to activate and potentiate effect of antibiotics as well as together with antibiotic treatment to reduce/prevent bacteria antibiotic resistance formation and to stimulate tissue healing and immune response.

Treatment can be combined with use of antibiotics and disinfectants for synergist antipathogen effect. For example, the use phototherapy with chlorhexidine to target biofilms is new to oral disinfection. The results of dual wavelength photodynamic therapy with chlorhexidine against *Streptococcus mutans* biofilm shown in appendix III are completely new. The use of high and low energy photons with photosensitizer increased substantially the antibacterial effect against biofilm and thus provides promising new approach for improvement biofilm treatment. The effectivity is based on photon and anionic photosensitizer ability to penetrate deeper into biofilm and provide efficient bacteria killing inside the biofilm as well as on the surface. The chlorhexidine effect is mostly present only on the surface of the biofilm. High energy photons reduce the biofilm EPS matrix formation that further increases the chlorhexidine effectivity in subsequent treatments.

Possible application methods of active ingredient to target site consist of aqueous solution, alcohol containing solution, chlorhexidine containing solution, hydrophilic gel, hydrophobic gel, hydrophilic polymer, hydrophobic polymer, paste, lotion, tape, plaster or band-aid.

Aqueous solutions of the above kind include mouth rinses. In particular, photosensitizer is used with a chlorhexidine solution or mouth wash.

In an embodiment, the benefit agent is delivered with a device that can be a film of lnm to 10 mm thick, gel, emulsion which can consist of polymers, inorganic molecular networks, nano/micro particles/fiber assemblies fiber networks, nonwovens, foams, hydrogels, paste or combination of these components.

The substrate with benefit agent can be attached, placed on top or inside or to be separate from the optoelectronic device applying the light.

In one embodiment, benefit agents like ICG are kept in hydrophobic or amphiphilic medium for better stability in storage and easy administering. This can be achieved by incorporating benefit substance in film or gel or into hydrophobic or amphipathic carrier liquid or gel. On of such application is a gel what has DMSO as main solvent. Dry gel consists of hydrophobic substance that has gel like characteristics for example gel where one ingredient is polydimethylsiloxane (PDSM). The gel can be categorized as slow drug release gel and active substance can be incorporated into gel independently or together with molecule categorized as antibiotic.

Film, gel or emulsion consisting of organic or inorganic polymer that has photosensitizer and possibly one or more potentiating compounds embedded. Film, gel and emulsion can have capillary function thus allowing water to enter when placed on moist surface. Film, gel and emulsion is transparent to treatment light. Film, gel or emulsion can consist of polymer that can be left on the treatment surface for subsequent treatment and for protection of site from other pathogens and dirt. Particular use of film, gel or emulsion is in treatment of aphthous stomatitis lesions, herpes sores and skin wounds.

Thin film, gel or emulsion can be partly or fully made to be water soluble wherein the water-soluble polymer is pullulan, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, Arabic gum, polyacrylic acid, methylmethacrylate copolymer, carboxyvinyl polymer, amylase, high amylase starch, hydroxypropylated high amylase starch, dextrin, pectin, chitin, chitosan, levan, elsinan, collagen, gelatin, zein, gluten, soy protein isolate, whey protein isolate, or casein.

Two light sources can be manufactured into same LED casing or incorporated into single light emitting surface. The emitted amount of between high energy photons and low energy photos can be from 50%-50% distribution to 1%-99% or vice versa 99%-1% or in between. Having low and high energy photons together contributes to more eye safe solution as the photons act through different mechanisms have different optical properties and total needed intensity is lower than only having high or low energy photons.

Based on the above, a first embodiment provides for an optoelectronic device capable of emitting high energy photons with majority energy between 2.8 eV and 3.5 eV and low energy photons with majority energy between 1.24 eV and 1.65 eV, with or without a photosensitizer, enabling a method for sustained antimicrobial effect in preventive and curative dental/oral care for long term use.

A second embodiment provides for an optoelectronic device of the afore-mentioned kind, where two wavelengths are emitted simultaneously or at a time interval of 100 ms from each other.

An optoelectronic device may comprise a light emitting component that has two or more light emitting surfaces (EPIs).

An optoelectronic device may also comprise has sensor capable of monitoring treatment progression, plaque amount. It is preferred that the optoelectronic device is capable of adjusting the treatment light based on the monitor feedback.

Different designs for optoelectronic devices are possible. The device can have tooth brush type shape, it can be a mouth piece or a rod like illuminator. The optoelectronic device used in treatment can incorporate micro-spectrometer sensors, temperature sensors, light sensors, pH sensors, force sensors, gyroscopes, and pressure sensors.

Based on the above, the present technology also provides a kit for treatment of microbial, viral or fungal infections of tissue, in biofilm, saliva, skin, plaque, on teeth surfaces and in mucous membranes. The kit comprises at least two components, viz. an optoelectronic component or device thereof and at least one photosensitizer. The optoelectronic component or device is capable of simultaneously emitting a first light consisting of high energy and a second light consisting of low energy photons. Typically, said first and said second light amount to at least 80% of all light emitted from the optoelectronic component or device. The photosensitizer is of a kind which can be activated by at least either of the high energy and low energy photons, preferably both. The photosensitizer can be of any of the above mentioned kinds. Thus, the photosensitizer of the kit is preferably provided in the form of Further, based on the afore-mentioned, the following represent preferred embodiments:

1. Method of monitoring dental plaque with high and low energy photons and plaque specific photosensitizer.
2. Method of embodiment 1 where low energy photons absorb to plaque specific photosensitizer detecting early plaque and high energy photons activate biofilm porphyrin molecules detecting old biofilm.
3. Method of embodiment 2 where photosensitizer is Indocyanine Green
4. Method of embodiments 1-3 where a filter is positioned between observer eyes or a detector component(s).
5. Method of embodiment 4 where a Specific filtering of 405/810 nm light can be used to enhance detection of autofluorescence, or detection of ICG light absorption or light emission abilities. The filtering can be located in front of the illuminating LED light source, or in front of a camera unit. The filtering can be low pass, high pass or band pass filtering or any of their combinations. Thus, one or several auto fluorescence can be detected and the information thereof combined.
6. Method of embodiment 1 where dual action of plaque can be used in plaque analysis. Measuring firstly the autofluorescence of the plaque using 405/810 peak LEDs with or without specific filtering, and secondly measuring the absorption of light by ICG with or without combining the light emission of ICG.
7. A device intended for photodynamic or photothermal therapy that is capable of detecting changes in therapy progression possibly, but not limited to, by monitoring photobleaching of the photosensitizer, thickness of the biofilm, density of the biofilm, pH of the biofilm and bacterial composition of the biofilm.
8. Sensor that can be used to monitor the thickness, density, dye binding and mechanical and chemical properties of the biofilm. Sensor can detect light absorption of one or more wavelengths and light emission of one or more wavelength or perform a fluorescence or absorption spectroscopy measurements.

9. Device may have one or more sensors and an algorithm that can inform user and adjust device operation based on the sensor feedback.
10. Sensor can monitor Indocyanine green photobleaching through NIR light absorption or fluorescence readout or both. Sensor can also monitor ratio of 405 nm absorption to ICG absorption. Biofilm thickness, density and bacteria composition can be valuated based on ICG absorption and rate of photobleaching during treatment. Bacteria and biofilm composition can be measured by the ratio of 405 nm light absorption and 780 nm, 810 nm light absorption.
11. The state of ICG in water phase and bound phase can be evaluated by 780 nm and 810 nm absorption ratio. PH of the bacteria biofilm can be estimated based on the shift in ICG absorption spectrum.
12. ICG fluorescence of wavelengths of 810 nm and 830 nm and their ratio can be used to detect free ICG and bound ICG and detect the sites of antibacterial activity.
13. Device can utilize or generate a changing electric field at the site of ICG absorption measurement to observe mechanical and chemical properties of the biofilm.
14. Device with the sensor can have algorithm and additional sensor not limited to gyroscopes that allow the determination of place of the treatment area and can pinpoint sensor readings to that site.

Other preferred embodiments are represented by

1. A composition comprising a photo-sensitive compound and a media, said media comprising:
(i) an aqueous phase;
(ii) high energy photons with majority energy between 2.8 eV and 3.5 eV; and
(iii) low energy photons with majority energy between 1.24 eV and 1.65 eV.
2. A composition comprising a photo-sensitive compound and a media, said media comprising:
(i) a PDMS gel;
(ii) a biofilm;
(iii) high energy photons with majority energy between 2.8 eV and 3.5 eV; and
(iv) low energy photons with majority energy between 1.24 eV and 1.65 eV.
3. The composition of embodiment 1 or 2, wherein said photo-sensitive compound is selected from the group consisting of photon absorption at the energy range of 1.24 eV and 1.65 eV.
4. The composition of any of embodiments 1 to 3, wherein the photo-sensitive compound is indocyanine green.
5. The composition of any of embodiments 1 to 4, wherein the photons have at least 50% of energy in 3.17 eV and 2.95 eV and 1.56 eV and 1.45 eV.

The following experiments illustrate the use of the present technology, in some embodiments further combined with dual light treatment:

EXPERIMENTAL

In a first series of tests, dye plaque specificity was observed in room light after treatment with hamamatsu 1394 and NIR light source.

Figure 2:
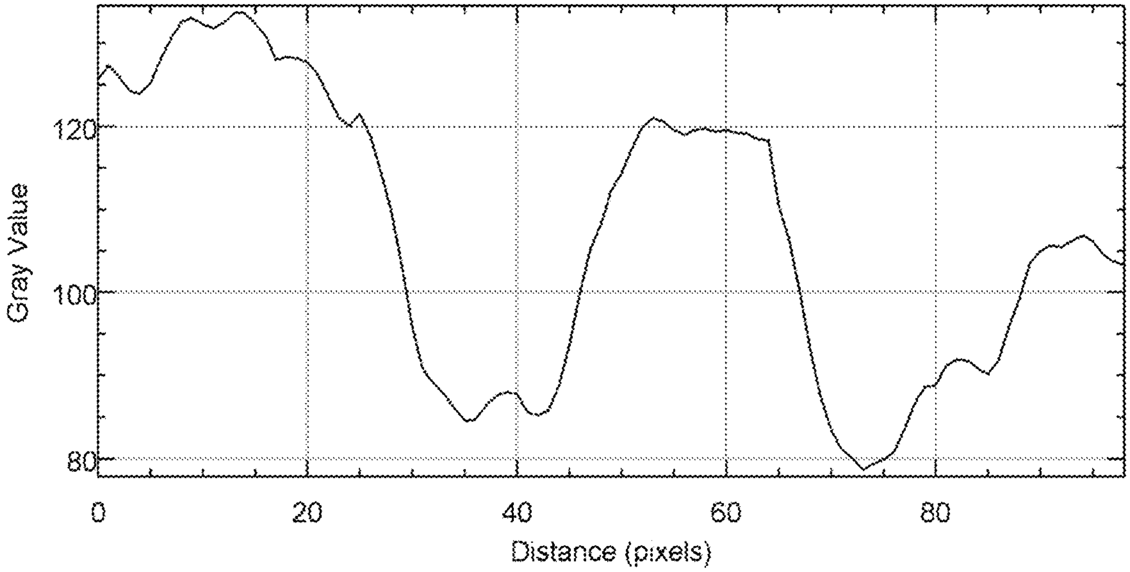
FIG. 2 is a diagrammatic depiction of gray level fluctuation to indicate dye light absorption.

As seen in FIGS. 1 and 2, respectively, there is distinct intensity difference between non-biofilm areas of the teeth and gums and the areas where biofilm is present.

Treatment can then be focused on the biofilm areas which are represented as dark in the FIG. 1 and with lower grey value in FIG. 2.

Figure 3:
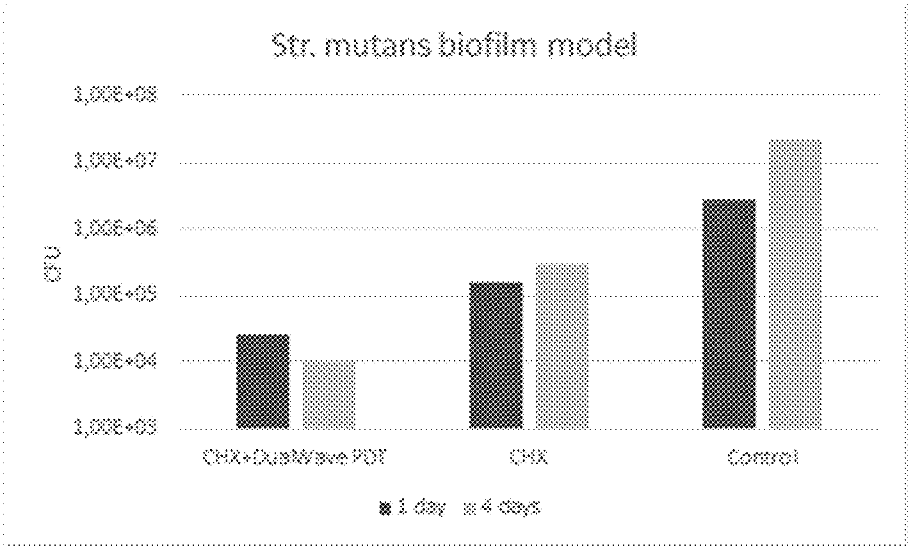
FIG. 3 is a bar chart showing the antimicrobial effect of chlorhexidine potentiated with dual wavelength PDT according to an embodiment of the invention.
Figure 4:
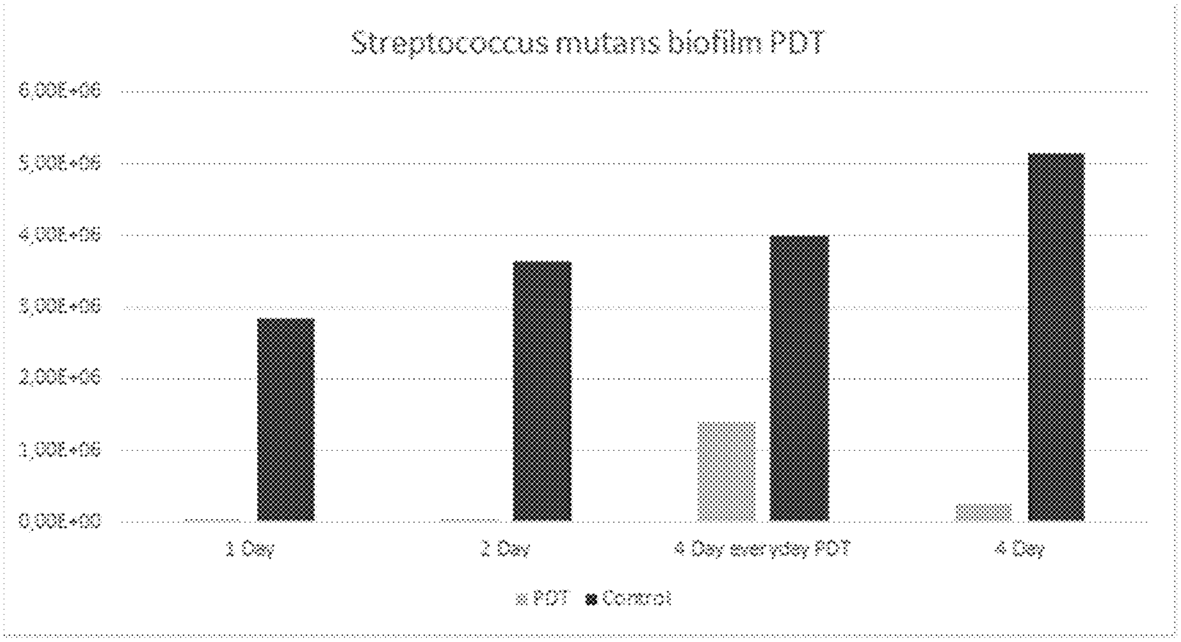
FIG. 4 is a bar chart showing the antimicrobial effect of PDT treatment on 1, 2 and 4 days old *Streptococcus mutans* biofilms.
Figure 5:
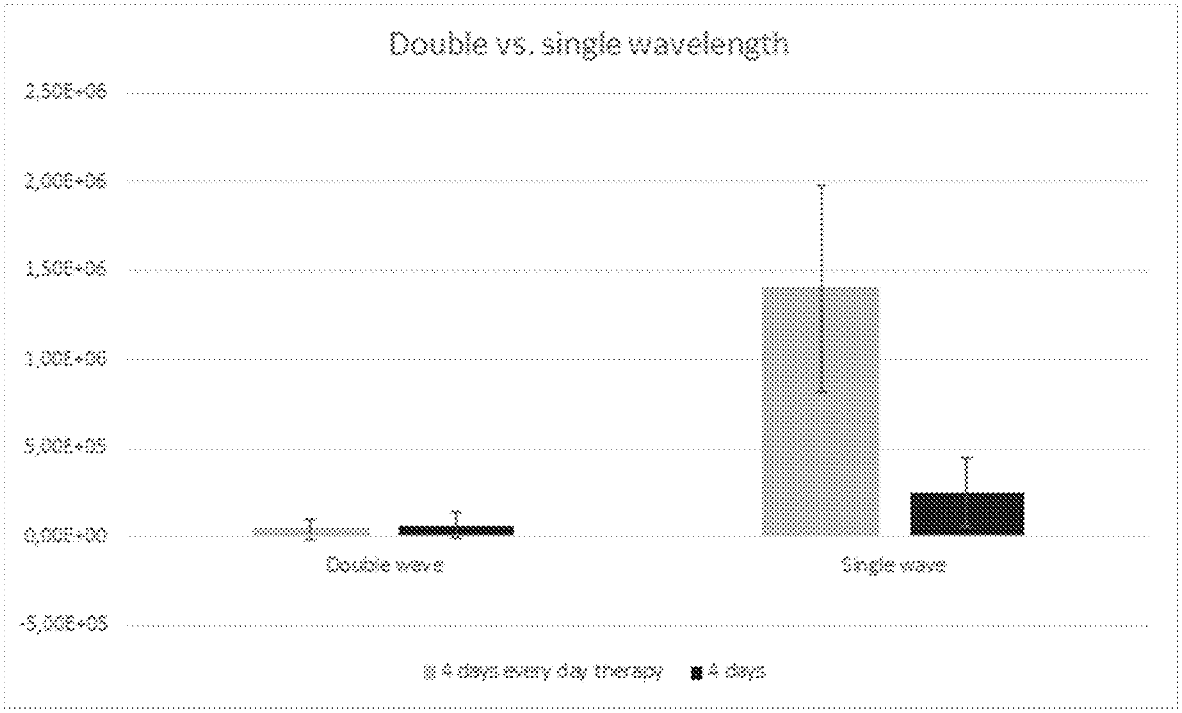
FIG. 5 is a bar chart showing the efficiency of double wavelength and single wavelength treatments on 4 days old biofilms.

In a second series of tests, potentiation of chlorhexidine with dual wavelength PDT was evaluated. The results are shows in FIG. 3 which indicates that the a combination of multi wavelength PDT with chlorhexidine gives a much stronger effect than reference and treatment with only one wavelength.

In a third series of test, the adaptability of *Streptococcus mutans* biofilms to multi and single wavelength PDT treatments, respectively, was compared.

Two separate monospecies biofilm model experiments were performed to study the effect of reoccurring photodynamic therapy on biofilm formation. The *Streptococcus mutans* biofilm experiments were divided in different classes based on biofilm age and the therapy given.

The one-time PDT treatment was performed for 1 day, 2 days and 4 days old biofilms. This effect was then compared to every day treated 4 days old biofilms with the hypothesis that the biofilm growth would be strongly suppressed in the everyday treated sample. The viability of the bacteria was assessed by serial dilution CFU method which was performed after the last photodynamic therapy treatment.

Materials and Methods

*Streptococcus mutans* (ATCC 25175) bacteria was grown over 18 h in growth chamber (36° C., 5% $CO_2$) in BHI-broth (Bio-Rad 3564014). The resulting bacteria suspension was diluted with 0.9% NaCl suspension to optical density of 0.46.

Biofilm was grown on bottom of well plate by adding 100 ul diluted *Streptococcus mutans* suspension in each well with 100 μl of BHI-broth growth medium. The bacteria plate was incubated in growth chamber (36 Celsius, 5% $CO_2$) and BHI-broth medium changed daily.

Exposure:

Before the light exposure, the growth medium was replaced with indocyanine green suspension which was let to incubate in dark in room temperature for 10 minutes. After the incubation the biofilm was washed twice with 0.9% NaCl solution. The treatment time was calculated from desired light amount and known intensity.

The light exposure was performed by placing the well plate under known LED light source. The given light intensity was analyzed with Thorlabs PM100D and S121C sensor head. Treatment time was changed to result in desired light amount.

CFU: After the exposure the biofilm was removed from the well by mechanically scraping it from bottom of the well plate using sterile inoculation rod. 100 μl of resulting bacteria suspension was then plated on BHI-plate with different dilution rations between 1:1 to 1:10 000.

Tests and Results

The first experiment of continuous treatment of *Streptococcus* biofilm with PDT was completed by using 250 μg/ml ICG with 810 nm light. Different age biofilms of 1 day, 2 days and 4 days were grown, and the treatment was given once to each biofilm to evaluate the effect of single time treatment to differently aged biofilms.

In addition to these three tests, a 4 day old biofilm was grown that was exposed to PDT treatment every day. The initial hypothesis was that everyday treated biofilm would have close to zero CFU. The results of single wavelength treatment are shown in FIG. 10 which shows the efficacy of the PDT treatment on 1, 2 and 4 days old *Streptococcus*

*mutans* biofilms. Two variants of 4 days old biofilm were done. One was exposed to PDT treatment every day and other only on a day 4.

The growth of total bacteria amount in controls as biofilm aged and the strong effect of PDT treatment to this biofilm model were as expected. The poor treatment effect in every day treated biofilm was surprising observation as it has been widely agreed that bacteria cannot develop resistance against photodynamic treatment. All of the above-mentioned experiments were repeated at least three times and 4 days every day treated biofilm was repeated 12 times to validate the finding.

A similar effect was not observed when a combination treatment was used. In this treatment the biofilm was targeted with combination of endo- and exogenous therapy. It was before shown in bacteria plate studies that 405 nm light at 70 J/cm$^2$ was needed to kill *Streptococcus mutans*. In dual combination experiment the red light (peak 810 nm) was combined with blue light (peak 405 nm). Multi light experiment focused to study the resistance inducing effect and thus it focused in 4 days old biofilm model with light treatment done daily and only on day 4. The hypothesis was that the everyday treatment would result in a poorest result as it was observed before. The experiment results are shown in FIG. 7.

Figure 7:
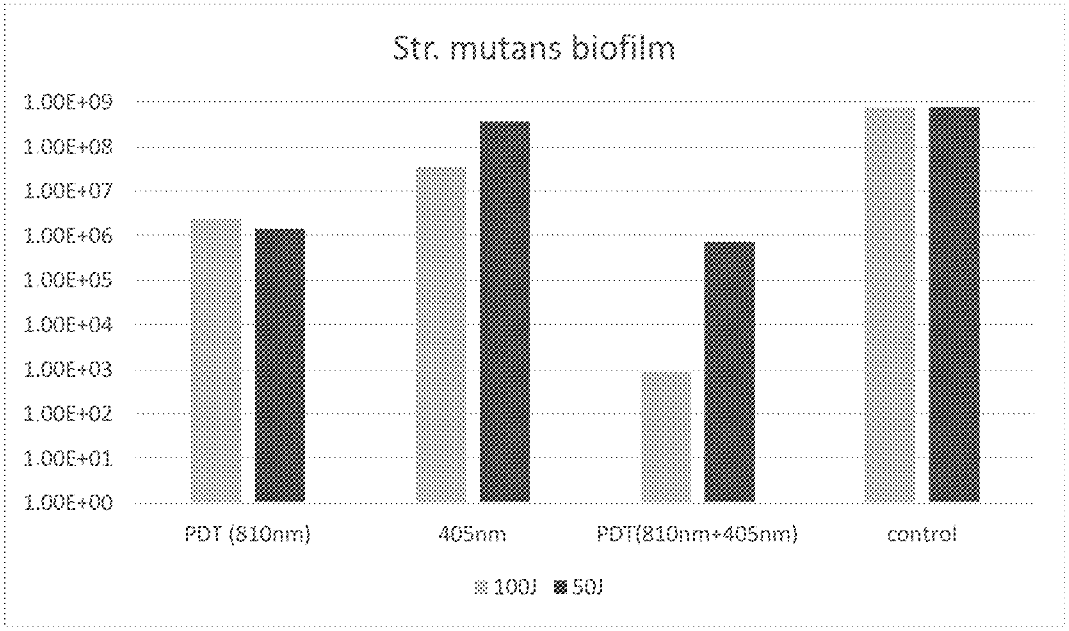
FIG. 7 is a bar chart showing the antimicrobial effect of PDT treatment after 14 days on *Streptococcus mutans* biofilms.

FIG. 7 is a bar chart showing a 4 days old biofilms treated with double wavelength and single wavelength PDT system, respectively. No significant difference of bacteria killing between every day therapy and 4 days therapy was observed in double wavelength system where as the single wavelength PDT failed to achieve strong bacteria killing in continuous treatment.

The treatment with dual wavelength combination light was thus more effective and no bacteria biofilm adaptation to the treatment was observed.

Figure 6:
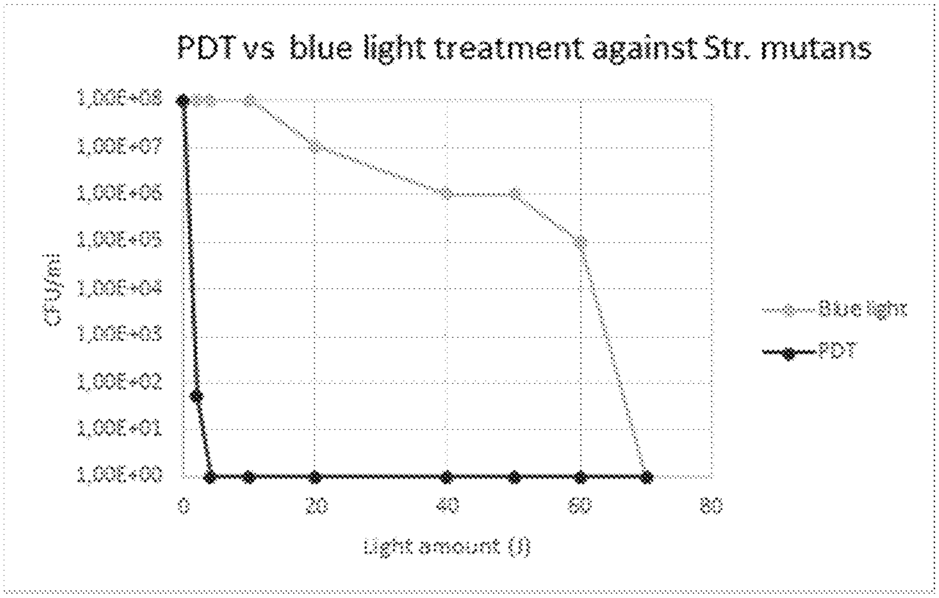
FIG. 6 is a chart showing the antibacterial effect of light having a wave length of 405 nm compared to PDT.

It would appear that a combination of endo- and exogenous photodynamic treatment simultaneously will increase the efficiency of biofilm targeted PDT. FIG. 6 shows the antibacterial effect of a treatment with 405 nm light compared to PDT.

As will appear, 405 nm light is not able to show strong effectivity against *Streptococcus mutans* until with high over 70 J/cm$^2$ energy density. For PDT the killing effect was much stronger. Already a dose of 4 J/cm$^2$ resulted in complete inhibition of *Streptococcus mutans* growth.

Finally it should be noted that in a fourth series of tests, similar results as above were obtained for treatment of Gram(−) bacteria.

Use of high and low energy photons with photosensitizer has better, more constant and robust antibacterial effect against gram positive and gram negative bacteria compared to traditional PDT which may lack effectivity against either gram negative or positive bacteria species as the different cell wall structures are susceptible for photosensitizers with different properties. Use of High and low energy photon treatment with active substance is recommended as it has minimal effect on the balance between gram negative and positive bacteria in the treatment area.

FIG. 7 is a bar chart showing the antimicrobial effect of PDT treatment after 14 days on *Streptococcus mutans* biofilms. The left-hand bar of each pair represents the result of light treatment at 100 J and the right-hand bar represent the result of light treatment at 50 J. As will become apparent, the present light treatment proves to be highly efficient against microbes.

INDUSTRIAL APPLICABILITY

The present invention can be used for detection carried out for cosmetic purposes as well as other non-therapeutic uses. It can also be used for antimicrobial and antiviral and antifungal detection and therapy. Thus, generally, viral or fungal infections in biofilm, plaque and on teeth surfaces can be detected and optionally treated.

The invention claimed is:

1. A method of detecting dental plaque, comprising:

subjecting a dental area of interest to high and low energy photons in the presence of a plaque specific photosensitizer, wherein the subjecting comprises subjecting the dental area of interest to a first light having a peak wavelength of 405 nm±10 nm, comprising the high energy photons, and to a second light having a peak wavelength of 810 nm±10 nm, comprising the low energy photons, wherein the dental area of interest includes plaque that absorbs the low energy photons in the presence of the plaque specific photosensitizer for detection, and biofilm comprising intracellular and extracellular fluorescent porphyrin molecules that absorbs the high energy photons for detection;

measuring, in response to the first light, the second light, or both, a first absorption of light of free plaque specific photosensitizer in liquid phase;

measuring, in response to the first light, the second light, or both, a second absorption of the plaque specific photosensitizer adsorbed to the dental area of interest;

determining a shift in an absorption spectrum of the plaque specific photosensitizer based on the first absorption and the second absorption; and determining a pH of the biofilm based on the shift in the absorption spectrum of the plaque specific photosensitizer;

wherein the plaque specific photosensitizer comprises indocyanine green (ICG).

2. The method according to claim 1, further comprising, prior to subjecting the dental area of interest to the high energy photons and the low energy photons, adsorbing the plaque specific photosensitizer to the dental area of interest and then subjecting the dental area of interest, sequentially, first to the high energy photons and then to the low energy photons.

3. The method according to claim 2, wherein the subjecting comprises directing the high energy photons and the low energy photons to the dental area of interest to achieve auto-fluorescence of said dental area of interest and fluorescence of said dental area of interest; and detecting the auto-fluorescence and the fluorescence generated in response to the high energy photons and the low energy photons.

4. The method according to claim 1, wherein the subjecting comprises adsorbing the plaque specific photosensitizer to the dental area of interest and subsequently subjecting the dental area of interest containing the adsorbed plaque specific photosensitizer to the high energy photons and the low energy photons simultaneously.

5. The method according to claim 1, further comprising detecting auto-fluorescence generated by the intracellular and extracellular fluorescent porphyrin molecules.

6. The method according to claim 1, further comprising adsorbing the plaque specific photosensitizer to the dental area of interest from a liquid composition comprising said plaque specific photosensitizer.

7. The method according to claim 6, wherein the liquid composition contains 0.00001 to 10% by weight of the plaque specific photosensitizer.

8. The method according to claim 1, further comprising detecting auto-fluorescence and/or fluorescence from the dental area of interest by using a filter positioned in the light path from the dental area of interest to a detector.

9. The method according to claim 8, wherein the filter is located in front of a camera unit.

10. The method according to claim 8, wherein the filter comprises one or more filters selected from the group consisting of low pass filters, high pass filters, band pass filters, and combinations thereof.

11. The method according to claim 8, comprising detecting auto-fluorescence at one or more wavelengths.

12. The method according to claim 1, wherein the subjecting further comprises:

subjecting the dental area of interest to the first light having the peak wavelength of 405 nm±10 nm or the second light having the peak wavelength of 810 nm±10 nm or both, optionally simultaneously or sequentially, in the absence of the plaque specific photosensitizer;

measuring first autofluorescence generated by the dental area of interest in response thereto, optionally using filtering to distinguish predetermined auto-fluorescence;

after subjecting the dental area of interest to the first light and the second light in the presence of the plaque specific photosensitizer, measuring second autofluorescence generated by the dental area of interest in response thereto, optionally using filtering to distinguish predetermined auto-fluorescence, wherein the first light and the second light are illuminated simultaneously or sequentially; and determining the ratio of the first and the second autofluorescence.

13. The method according to claim 12, further comprising determining adsorption rate, and optionally photobleaching rate, of the plaque specific photosensitizer.

14. The method according to claim 12, further comprising determining one or more parameters of the dental area of interest selected from the group consisting of biofilm thickness, biofilm density, biofilm bacterial composition, and combinations thereof.

15. The method according to claim 1, wherein the subjecting further comprises subjecting the dental area of interest to light having a peak wavelength of 780 nm and determining the light absorption of the plaque-specific photosensitizer.

16. The method according to claim 1, further comprising:

measuring fluorescence of the plaque specific photosensitizer from the second light, subjecting the dental area of interest to a third light having a peak wavelength of 830 nm±15 nm, measuring fluorescence of the plaque specific photosensitizer from the third light, and determining a ratio of the fluorescence of the plaque specific photosensitizer from the second light and the third light for determining a value of free ICG and bound ICG and for detecting sites of antibacterial activity.

17. The method according to claim 16, wherein hyperspectral imaging or spectroscopy is used for plaque detection or analysis.

18. The method according to claim 1, wherein an external stimulus to dental plaque is given in form of electromagnetic radiation, electric field, chemical or mechanical energy or a combination thereof while monitoring changes in fluorescence properties.

19. The method according to claim 1, wherein the quantity or quality, or both, of the dental pellicle is detected, determined or analysed.

20. The method according to claim 1, further comprising generating an image by using a sensor and an algorithm.

21. The method according to claim 1, wherein at least one of fluorescence intensity, total intensity, reflected intensity, or auto-fluorescence intensity is measured.

22. The method according to claim 1, further comprising detecting auto-fluorescence and/or fluorescence from the dental area of interest.

23. A method of detecting dental plaque, comprising:

(a) illuminating a dental surface within the oral cavity of a subject in the presence of a plaque specific photosensitizer with a first light having a peak wavelength of 405 nm±10 nm;

(b) illuminating the dental surface with a second light having a peak wavelength of 810 nm±10 nm;

wherein the dental surface includes plaque that absorbs the low energy photons in the presence of the plaque specific photosensitizer for detection, and biofilm comprising intracellular and extracellular fluorescent porphyrin molecules that absorbs the high energy photons for detection, wherein the plaque specific photosensitizer comprises indocyanine green (ICG);

the method further comprising:

(c) measuring one or more optical signals generated from the dental surface in response to illuminating steps (a) and (b), wherein the one or more optical signals comprise at least one of fluorescence emitted from the dental surface, light reflected from the dental surface, or light absorbed at the dental surface, wherein (c) includes:

measuring, in response to the first light, the second light, or both, a first absorption of light of free plaque specific photosensitizer in liquid phase;

measuring, in response to the first light, the second light, or both, a second absorption of the plaque specific photosensitizer adsorbed to the dental surface; and (d) determining the presence of dental plaque based on the measured optical signals using a ratio, difference, or spectral profile of the one or more optical signals, wherein (d) includes:

determining a shift in an absorption spectrum of the plaque specific photosensitizer based on the first absorption and the second absorption; and determining a pH of the biofilm based on the shift in the absorption spectrum of the plaque specific photosensitizer.

* * * * *